United States Patent [19]

Curry et al.

[11] 4,271,123
[45] Jun. 2, 1981

[54] AUTOMATED SYSTEM FOR PERFORMING FLUORESCENT IMMUNOASSAYS

[75] Inventors: Robert E. Curry, Novato; Michael G. Simonsen, San Rafael; Eric D. Schwartz, Richmond, all of Calif.

[73] Assignee: Bio-Rad Laboratories, Inc., Richmond, Calif.

[21] Appl. No.: 87,275

[22] Filed: Oct. 22, 1979

[51] Int. Cl.³ .......................................... G01N 33/54
[52] U.S. Cl. ................................. 422/64; 23/230 B; 23/915; 422/67; 364/497
[58] Field of Search ............... 23/915, 230 B; 422/64, 422/65, 67, 56; 250/458, 461 B; 364/497, 498

[56] References Cited

U.S. PATENT DOCUMENTS

| | | | |
|---|---|---|---|
| 3,728,079 | 4/1973 | Moran | 422/65 |
| 4,043,756 | 8/1977 | Sommervold | 422/64 X |
| 4,150,949 | 4/1979 | Smith | 23/230 B |
| 4,153,675 | 5/1979 | Kleinerman | 23/915 |
| 4,170,625 | 10/1979 | Welch | 422/64 |
| 4,201,763 | 5/1980 | Monthony et al. | 23/230 B |

*Primary Examiner*—Ronald Serwin
*Attorney, Agent, or Firm*—Townsend and Townsend

[57] ABSTRACT

A sample analyzer for quantitating relatively small amounts of clinically significant compounds in a liquid sample together with a sample mixing device (sampler) is disclosed. The analyzer has a transparent cell for holding the liquid sample. A light source focuses a stable light beam onto the sample so that fluorescent particles in the sample cause fluorescent emissions, the intensity of which is a function of the intensity of the light beam and the concentration of fluorescent particles in the sample. A detector in optical communication with the cell receives and senses photons forming the fluorescent emissions of the particles when excited by the light beam. The sampler holds a multiplicity of vials in an upright position in a row, advances the vials in incremental steps to present them at an aspiration station and includes an aspirator having a downwardly open suction tube that is vertically inserted into and withdrawn from the vials. A vacuum source withdraws the liquid sample from the vials through the suction tube and flows it to the sample cell in the analyzer. A mixer surrounds the suction tube and is activated before the sample is withdrawn form a uniform suspension.

51 Claims, 23 Drawing Figures

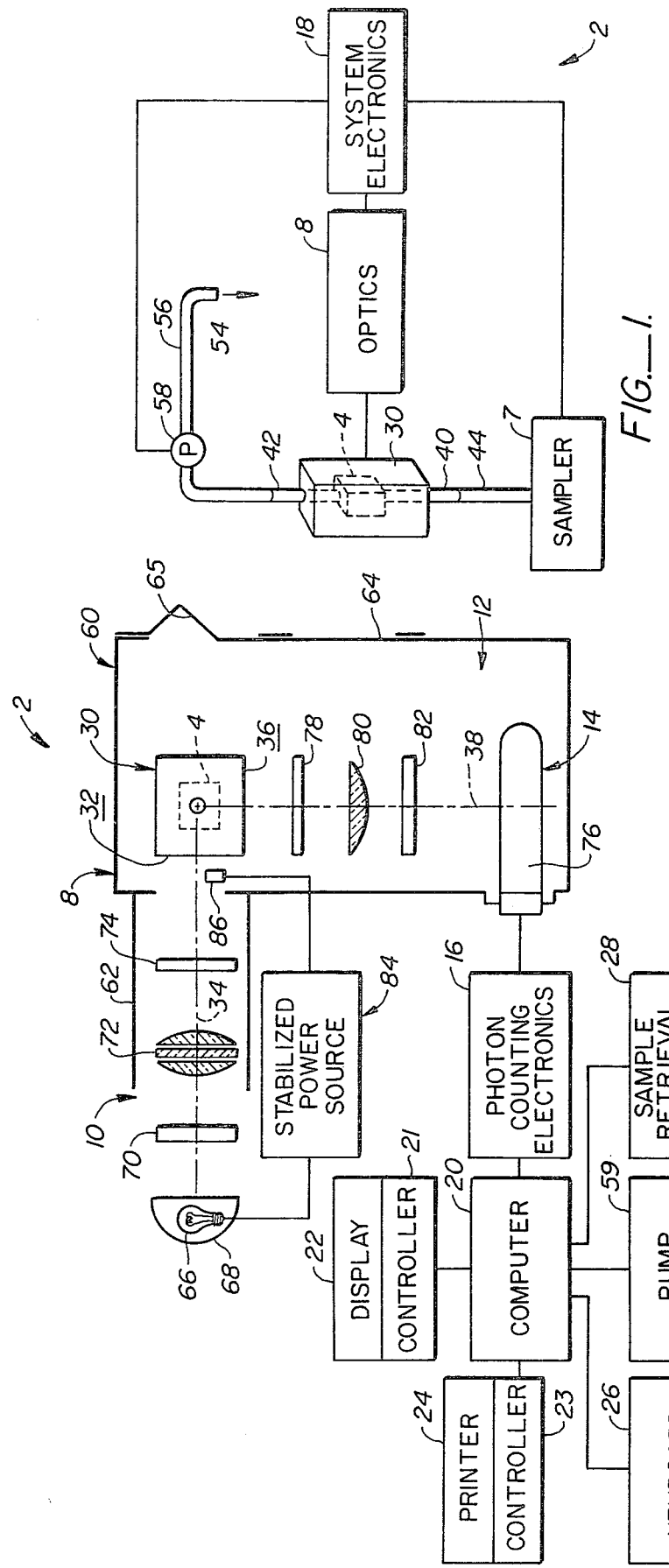

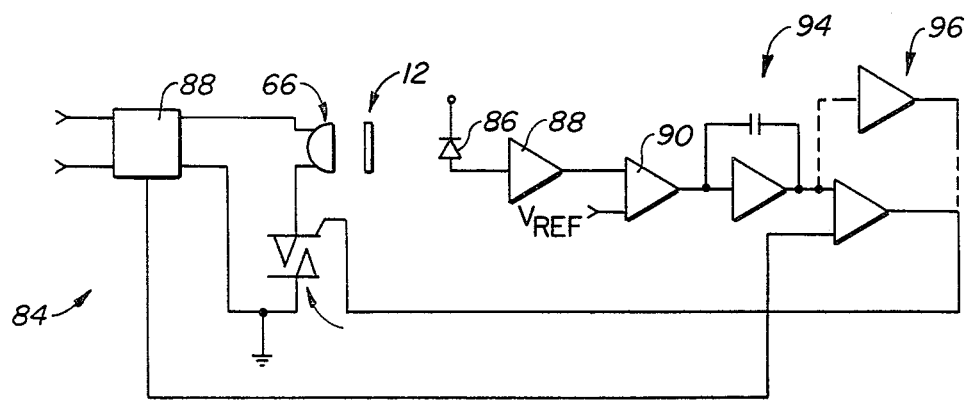
FIG._3.
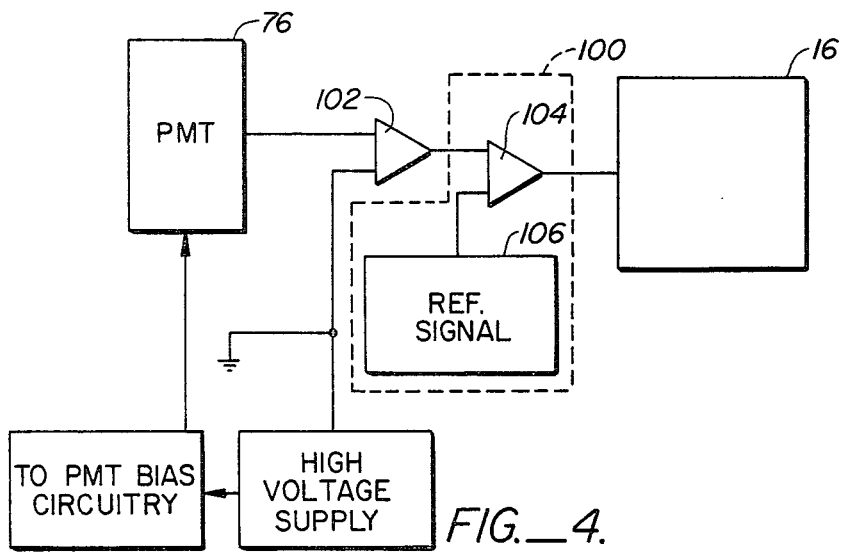
FIG._4.
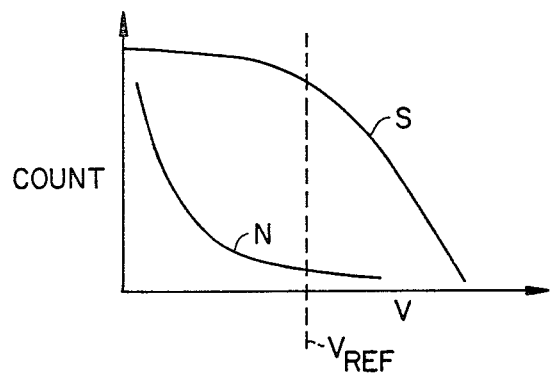
FIG._5A.

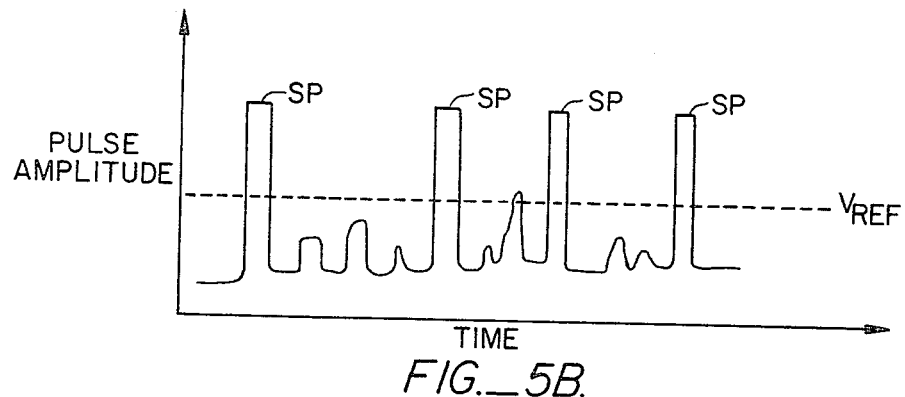
FIG._5B.
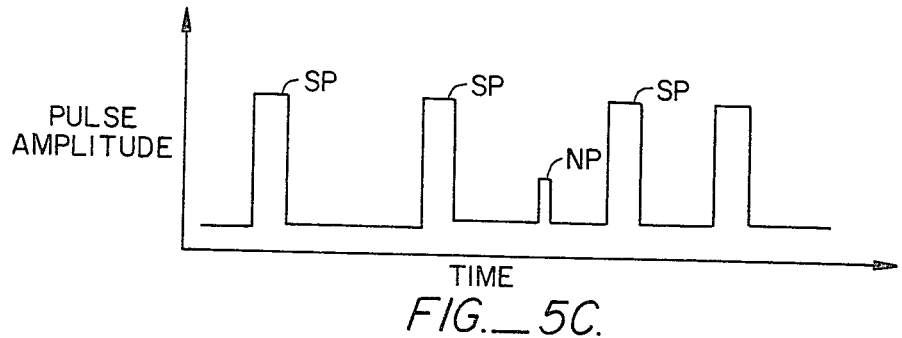
FIG._5C.
FIG._8.

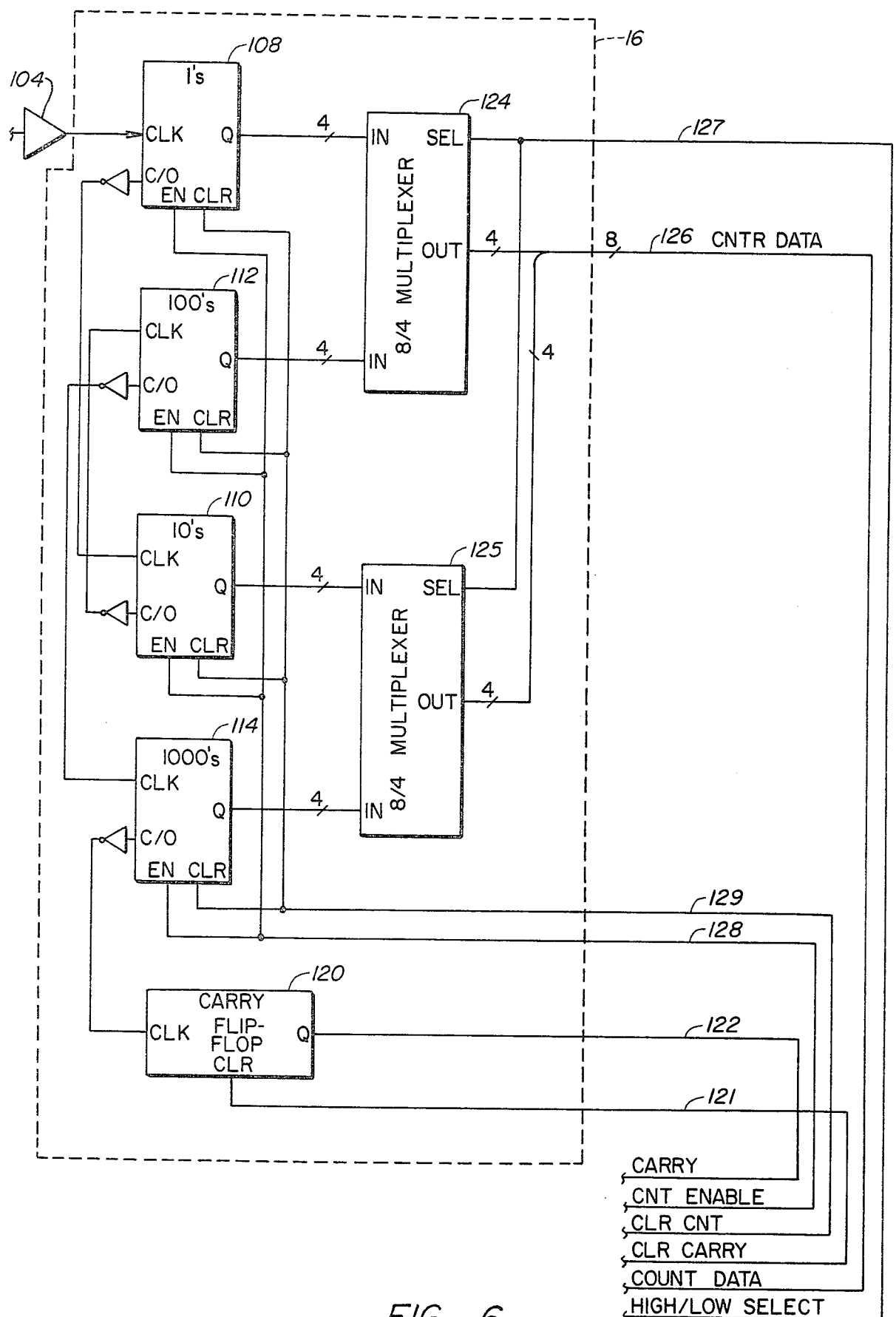
FIG._6.

| FIG. 7A. | FIG. 7B. |
|---|---|

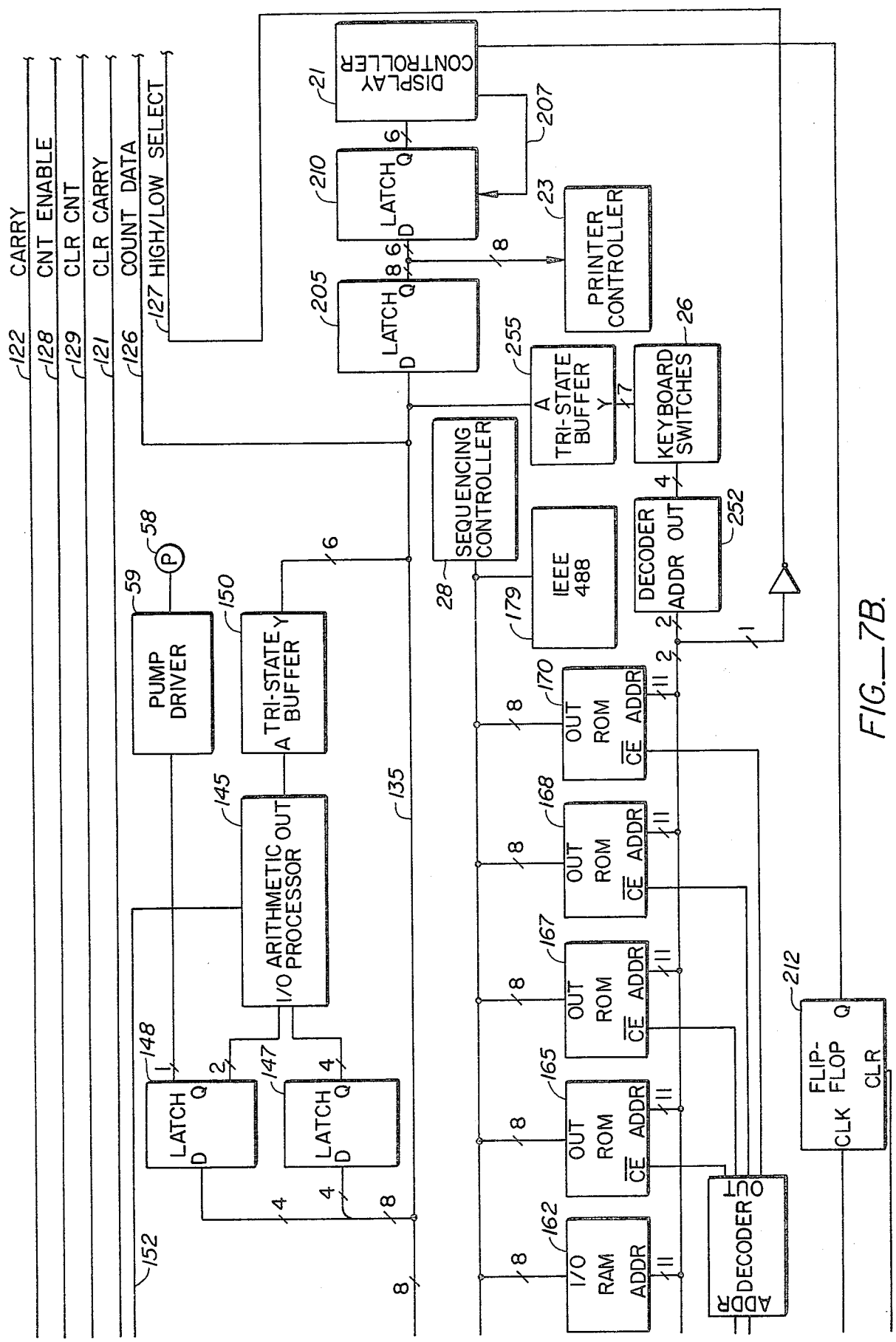
FIG._7B.

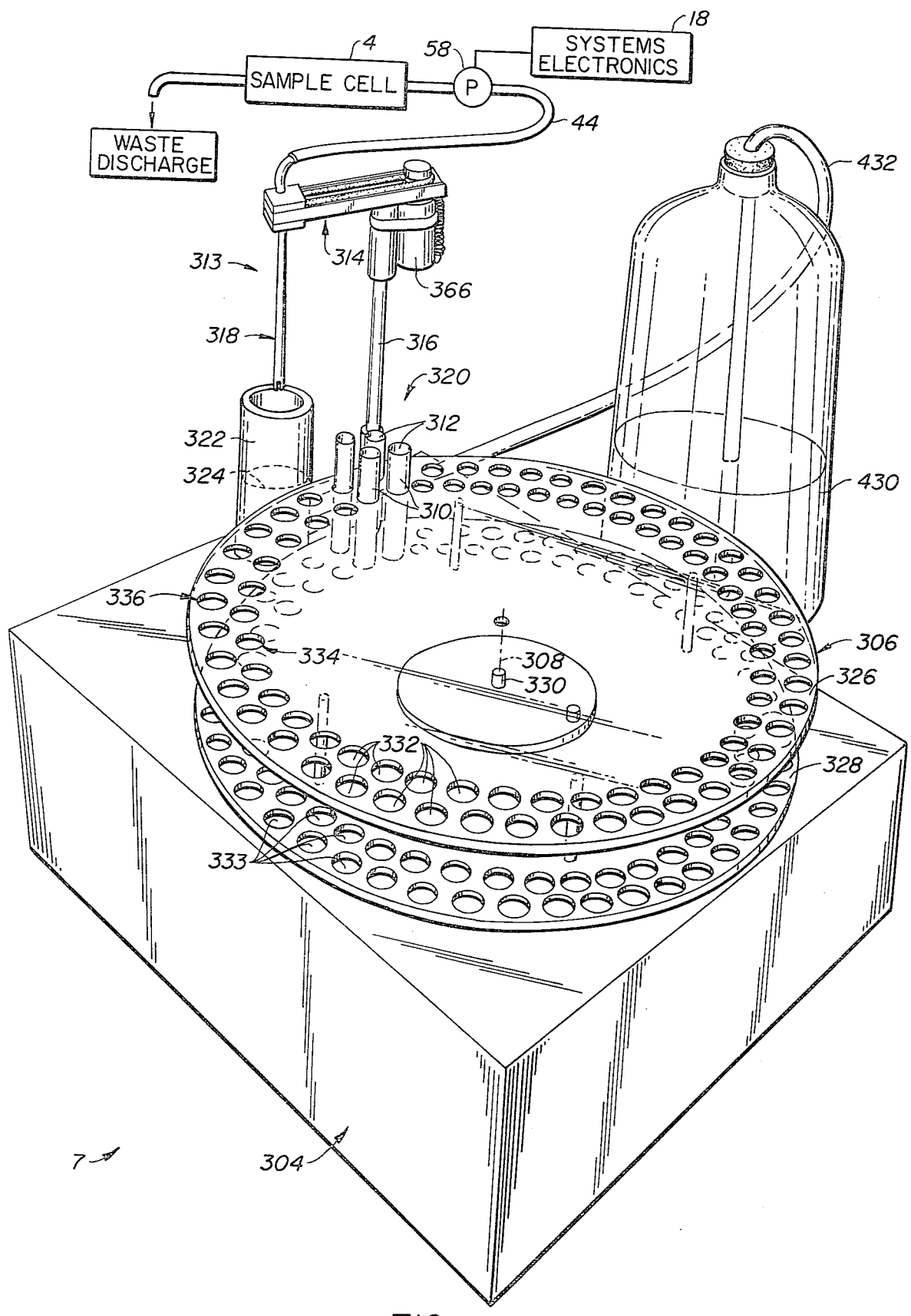
FIG._9.

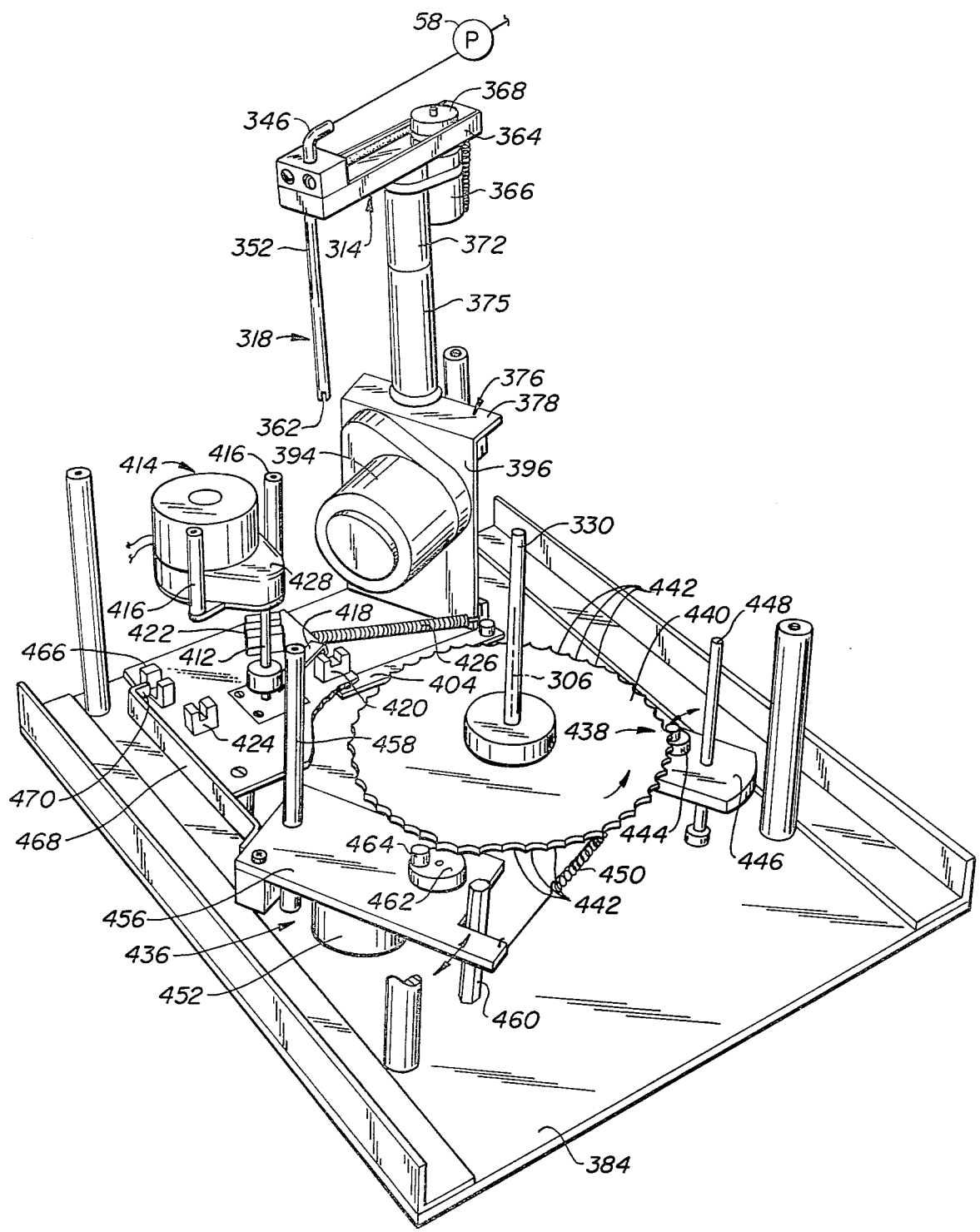
FIG._10.

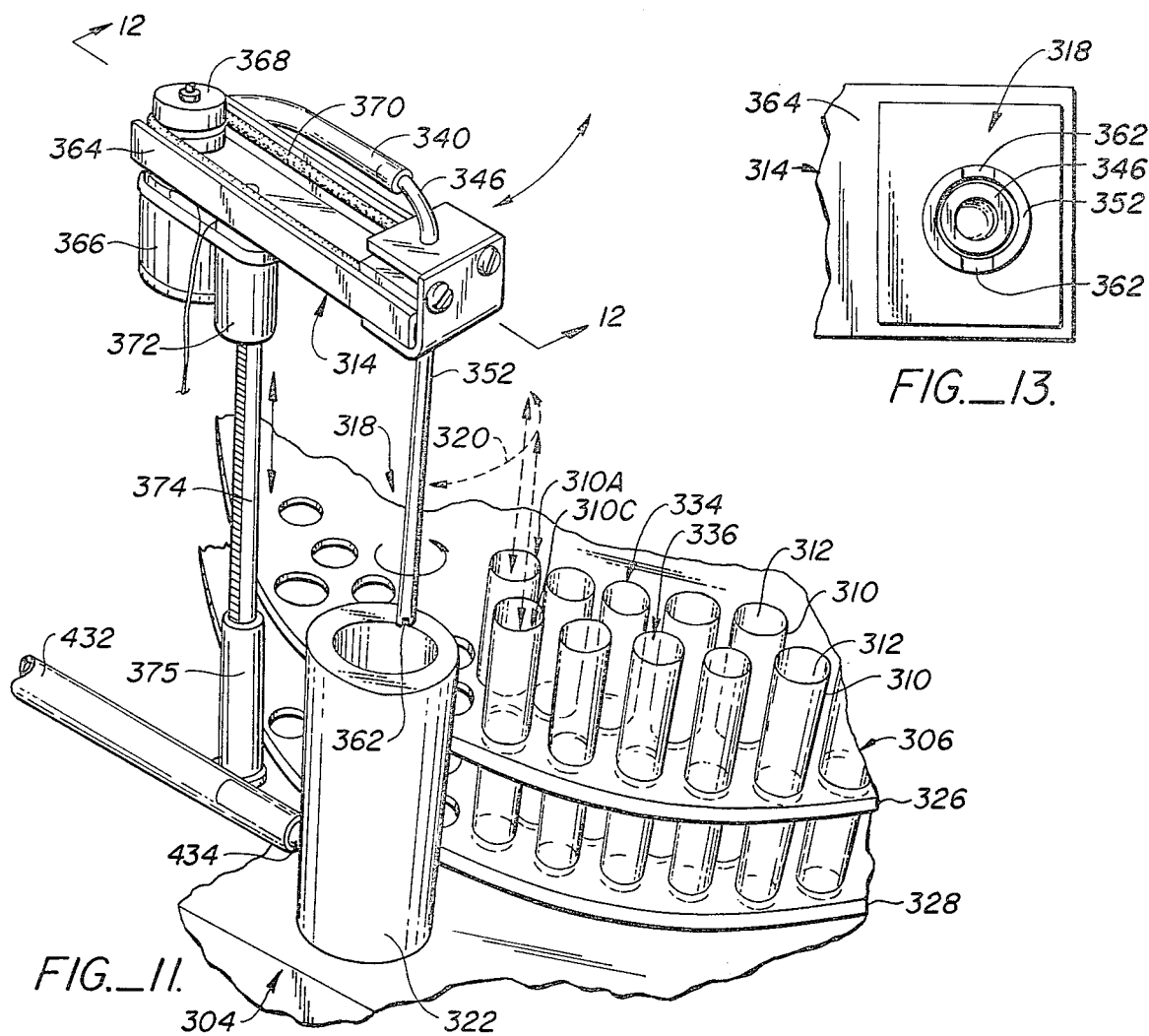
FIG._11.
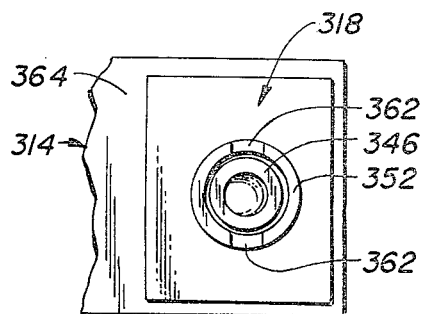
FIG._13.
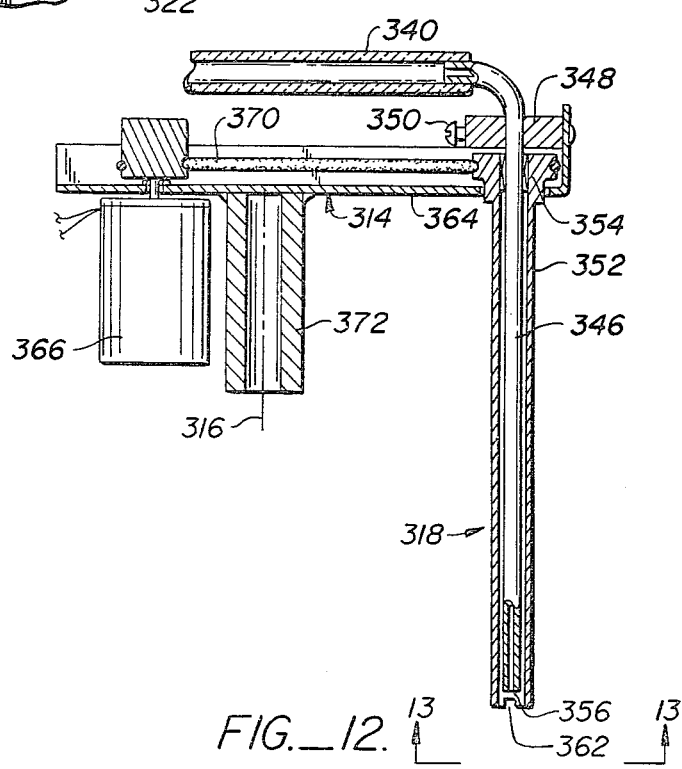
FIG._12.

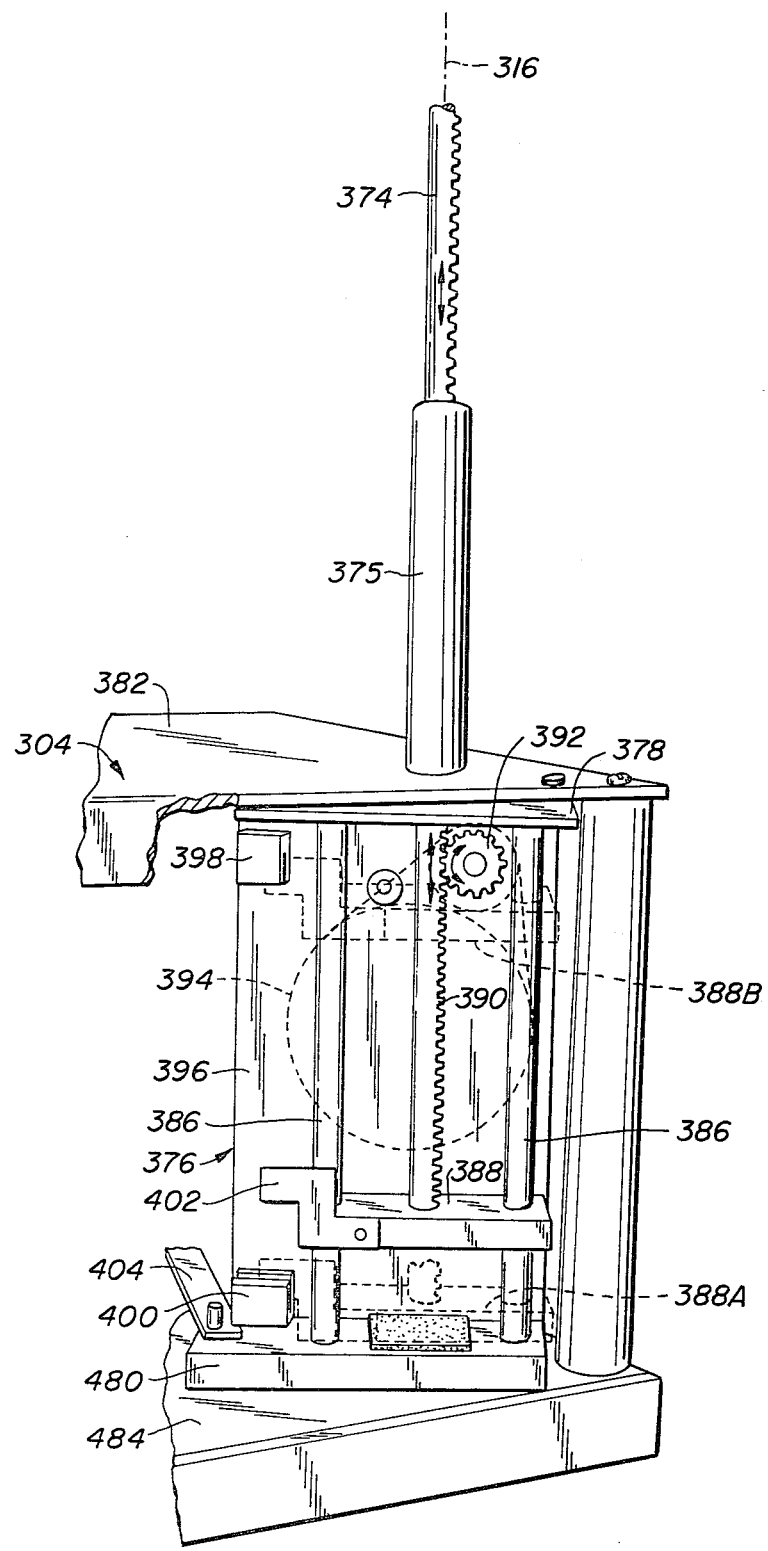
FIG._14.

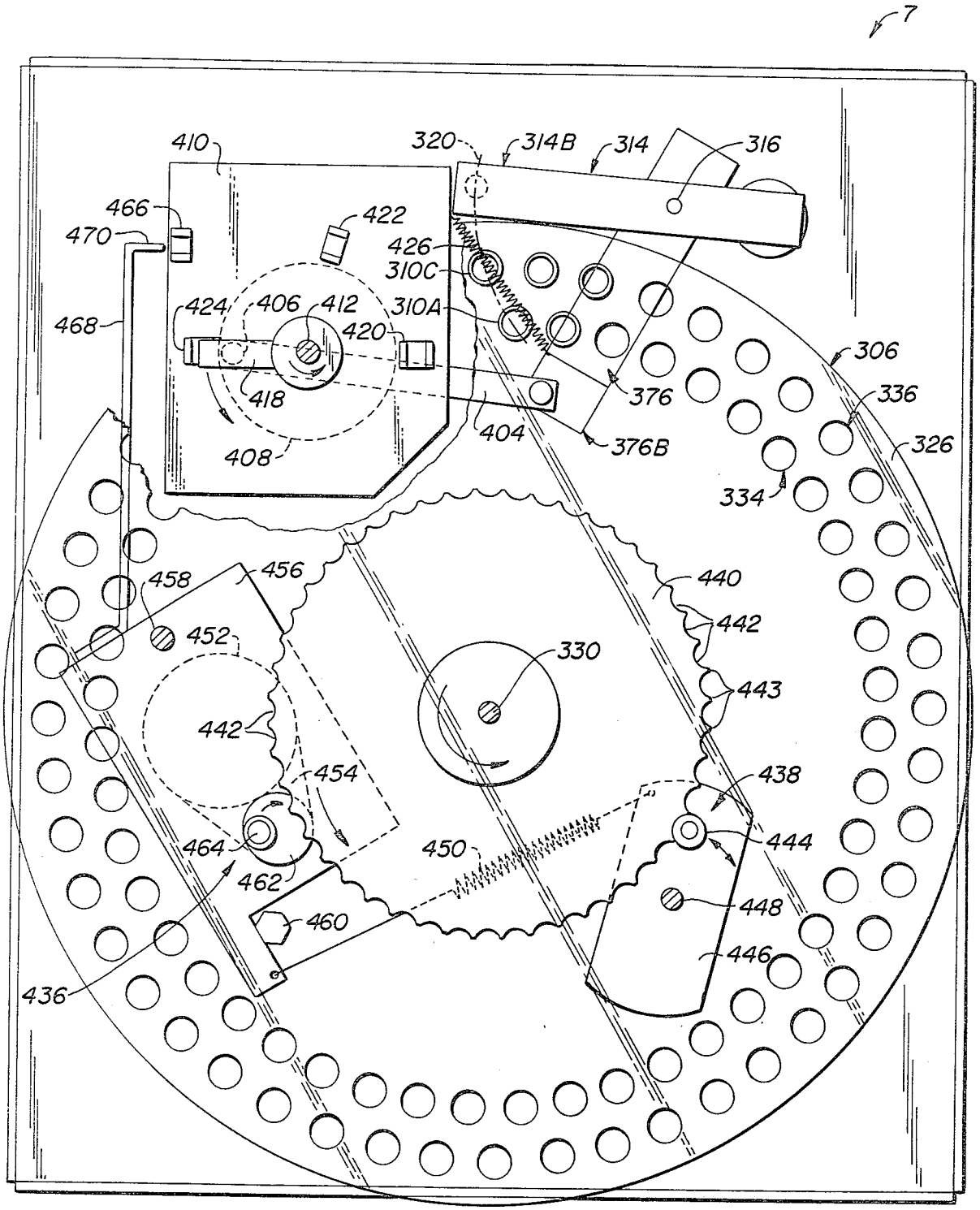
FIG._15.

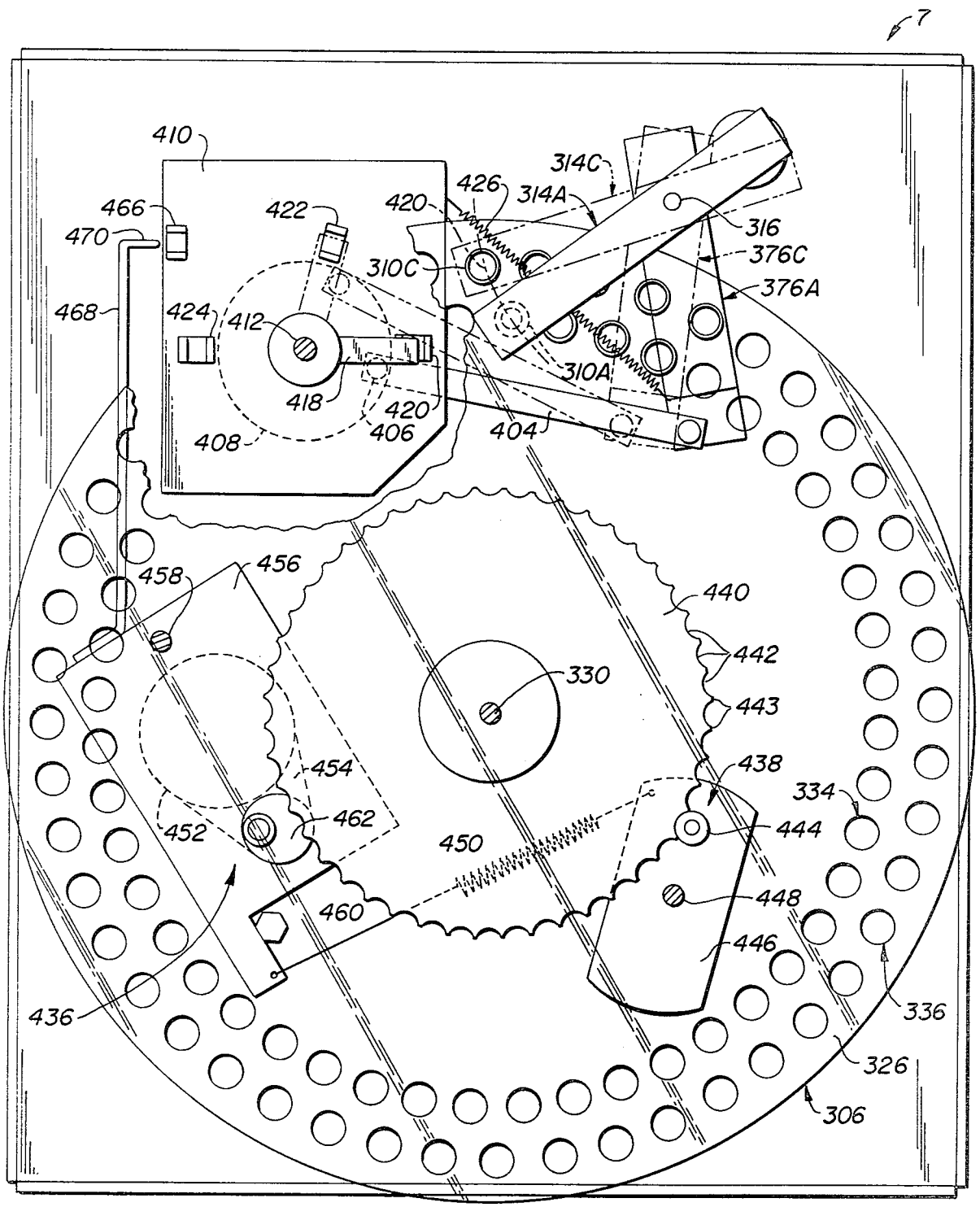
FIG._16.

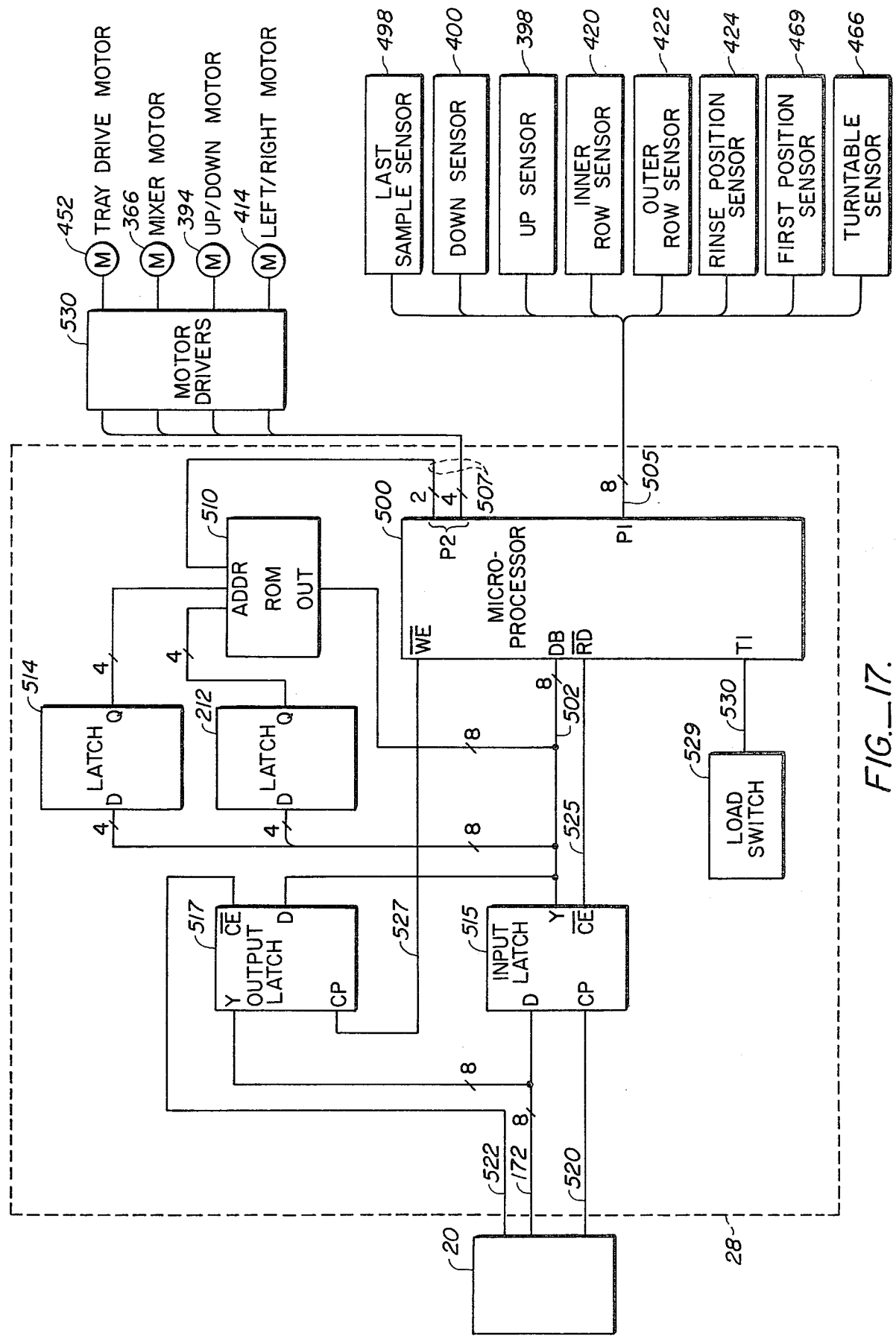
FIG._17.

AUTOMATED SYSTEM FOR PERFORMING FLUORESCENT IMMUNOASSAYS

BACKGROUND OF THE INVENTION

The present invention relates to an automated system for the immunoassay of subnanogram quantities of certain compositions by molecular fluorescence.

The quantitative determination of small amounts of clinically significant compounds, such as metabolites, hormones, drugs and proteins are of recognized diagnostic importance. Radioimmunoassay (RIA) has become the standard method for making such determinations because of its sensitivity and specificity.

However, RIA has certain drawbacks. The radioactivity associated with RIA may present psychological or physical health hazards to the technologists, requires special licensing from nuclear regulatory agencies, requires the special disposal of wastes, limits the useful life of a reagent kit to a few months at the most, and requires relatively expensive instrumentation. To circumvent these drawbacks, alternative methods including fluorescence immunoassay (FIA) have been developed.

FIA is a technique in which a fluorescent molecule is substituted for the radioactive label used in RIA. Some of the advantages of FIA are: no radioactivity, a much longer useful lifetime of the test components or chemicals necessary for the assay, and relatively less expensive instrumentation for performing the assays.

By way of background, the commonly owned co-pending U.S. patent application bearing Ser. No. 875,475, filed Feb. 6, 1978 for SOLID PHASE IMMUNOFLUORESCENT ASSAY METHOD, now U.S. Pat. No. 4,201,763, describes in detail a FIA method for antigens (or haptens) and their antibodies through the use of an immune reactant related to the antibody or antigens to be determined which is covalently bonded or coupled to polymeric particles whose size permits direct measurement of a labelled immunological reagent's fluorescence in an aqueous suspension thereof by direct optical spectroscopy. A key to the method described in that U.S. patent application lies in the selection of certain types of polymeric particles in sizes which provide a substantially homogeneous suspension during execution of the assay. It has been discovered that such a condition exists and that direct fluorometric measurements can be made when the polymeric particles have a size of about 0.1–10 microns.

Utilizing such particles, an appropriate immune reactant immunologically related to unknown antigen or antibody to be determined is covalently bonded thereto. The particles, unknown immune reactant, and appropriate fluorescently labelled immune reactant are mixed under conditions so that a quantity of the labelled immune rectant proportional to the concentration of the unknown immune reactant is immunologically bound, directly or indirectly, to the particles.

In accordance with said co-pending U.S. patent application, the FIA provides water insoluble hydrophilic polymeric particles of about 0.1–10 microns in size and having covalently bonded thereto the immunological homolog for an antigen or antibody to be determined. The particles are combined with the antigen or the antibody to be determined in an aqueous solution to form an immunological bond therebetween. A fluorescently labelled antigen or antibody corresponding to the antigen or antibody to be determined is immunologically bound to the particles.

Any suitable water insoluble polymeric particle may be utilized in the FIA described in said U.S. patent application. Generally, the particle will be in spherical or bead form and will be selected from polymers which can be derivatized to give a terminal primary amine, terminal carboxyl, or hydroxide group. The antibody or antigen is then immobilized on the particle under conventional reaction conditions to produce a covalent bond therebetween. Useful polymeric particles are formed, for example from crosslinked polyacrylamides. Other suitable polymeric particles are described in said U.S. patent application and in the references cited therein.

The particles are then physically separated, usually by centrifuging them, typically at 1500 g to pack the particles at the bottom of the test tube into a pallet. The supernatant is decanted, to the extent necessary the tube or vial is blotted dry and a barbital buffer is added to the pellet in the test tube to reconstitute it and resuspend the particles to form a suspension which includes the fluorescent particles.

The suspension is then analyzed on a fluorometer to determine the concentration of fluorescent particles in the sample to obtain information from which unknown antigen or antibody can be determined.

As has been customary in the past, these tests have heretofore been performed manually one after the other. This required, inter alia, a vigorous manual shaking of the test tube to reconstitute each pellet and resuspend the fluorescent particles. To obtain an accurate test it is, of course, necessary that the suspension be uniform which prolonged the time during which the tube had to be shaken. Thereafter, the sample was fluorometrically analyzed, either in the test tube or by pouring it from the tube into a suitable container of a fluorometer.

This procedure is time-consuming and requires the constant close supervision by a highly skilled technician. More importantly, it gives no assurance that an adequate mixing of the sample has taken place. Without such mixing, however, the ultimate readout is inaccurate and can render the entire test of questionable value. Further, the test is relatively expensive because of the close and constant supervision it requires.

A key to the success of FIA is the reliability and accuracy of the fluorometer over extended periods of time. In this regard, prior art fluorometers had certain shortcomings which could affect the ultimate readout and thus compromise the accuracy of the test. Conventional fluorometers that operate in an analog mode are unsatisfactory because of the relative insensitivity of such fluorometers when measuring the low light intensities encountered when performing FIA.

Better accuracy can be attained with photon-counting fluorometers which are relatively simple and inexpensive to construct. Robert E. Curry et al discuss the construction of photon-counting fluorometers (hereinafter "fluorometer" unless otherwise indicated) in "Design and Evaluation of a Filter Fluorometer that Incorporates a Photon-Counting Detector" on pages 1259–1264 of *Clinical Chemistry*, Vol. 19, No. 11, 1973, although the use of such fluorometers in conjunction with FIA has not heretofore been considered. The Article notes that photo-counting is an effective method for minimizing dark current contributions in photomultiplier tubes since electrons emitted from the dynodes are amplified less than electrons emitted from the photocathode and level discriminating circuitry can be used to differentiate between the dark current and photon signals.

For the determination of small amounts (i.e. from subnanomolar levels up) of clinically significant compounds by FIA, accuracy problems are, of course, not fully solved by employing a photo-counting fluorometer. Stray light, a non-uniform suspension of the fluorescent beads, light scattering, a variation in the magnitude of the samples' own fluorescence as well as changes in the primary light intensity all adversely affect the ultimate readout and lessen its accuracy. In addition, existing FIA methods must rely on an essentially manual, sample by sample determination of the fluorescence which requires the constant attention of highly skilled and, therefore, costly operations. This in turn has a tendency to drive up the already high costs for such tests.

SUMMARY OF THE INVENTION

The present invention provides an integrated system for conducting FIA on a large number of individual samples in an automatic, reliable, self-correcting and continuous manner for the quantitation of antigens or haptens and antibodies of any molecular weight and at concentrations from subnanomolar levels upwards. Initially, in one type of a competitive binding FIA, the antigen labeled with a fluorescent dye competes with the antigen in the sample or standard for a limited amount of antibody which is immobilized on a 0.1–10 micron polyacrylamide bead. After a suitable incubation, the labeled antigen bound to the antibody beads is separated from the free fluorescently-tagged antigen in the supernatant by centrifugation and decantation. After resuspending the antibody beads in buffer, the fluorescence bound to the beads is measured in accordance with the present invention in a sample analyzer that utilizes a feedback stabilized light source which illuminates a sample in a transparent holding cell to generate fluorescent emissions. The emissions are sensed by a photon-counting detector that forms photon generated output pulses from which background noise is effectively eliminated.

System electronics for the present invention employs large scale integration microcomputer architecture to provide an automated capability. In addition to supervisorial and sequencing tasks, the microprocessor performs data acquisition and data reduction operations to convert photon count information into antigen concentration. The apparatus of the present invention assures a measurement precision and accuracy of about one to three percent for the above indicated relatively low concentrations being measured.

The present invention also overcomes the disadvantages inherent in prior art procedures for reconstituting the pellets in the bottom of test tubes and especially for uniformly mixing the pellets with the buffer solution and for presenting the resulting suspension to a fluorometer so that it can be appropriately analyzed. The present invention accomplishes this by fully automating both the mixing and the withdrawal of the suspension from the vials so that they can be presented to the appropriate instrument such as a fluorometer.

The apparatus of the present invention is fully automated, being capable of processing one sample after the other on a continuing basis. For this purpose the analyzer includes a sample cell which is fluidly communicated with a suitable pump that transports a predetermined sample volume into the cell, maintains the volume in the cell until its fluorescence has been measured, and thereafter replaces the sample in the cell with a new one. The pump is operatively coupled with an automatic sample mixing and retrieving unit, hereinafter sometimes referred to as "sampler".

Generally speaking, the analyzer of the present invention provides an apparatus for quantitating relatively small amounts of a clinically significant compound such as thyroxine or triiodothyronine which has a transparent cell for holding a prepared liquid sample. A light source generates a stable light beam that is focused on the sample so that the beam causes fluorescent emissions by the particles in the sample. The intensity of the emissions is a function of the intensity of the light beam and the concentration of the fluorescent particles in the sample. A detector in optical communication with the cell receives and senses photons defining the fluorescent emissions by the particles when excited by the light beam. The number of sensed photons is counted and the total count from the sample (over a given time period) is a measure of the number of fluorescent particles in the sample.

The associated optics include a lens which focuses the light beam on the sample, a band pass filter which eliminates substantially all light from the light beam other than light having a wavelength which excites the particles and generates fluorescent emissions, and a heat absorbing filter in the optical branch between the light source and the sample. The branch of the optics between the sample and the detector includes a collecting lens, a cutoff filter to remove the excitation wavelength and thereby the effects of incoming light scattered by the sample, and a band pass filter which removes from the light received by the detector substantially all wavelengths other than the wavelength at which the particles fluoresce. The sample, the light source as well as the optics are mounted within a black housing which includes suitable light traps to prevent light scattering, secondary fluorescent emissions, etc. As a result, the detector receives substantially only fluorescent emissions caused by the light beam striking the fluorescent particles in the sample to assure that the emission, and in particular the photons of the emissions are the result of fluorescence caused by the light beam only. This significantly enhances the accuracy of the photon count by the detector.

To prevent fluctuations in the photon count due to changes in the intensity of the light beam the light source is stabilized. For this purpose, a photosensor such as a silicon photodiode is mounted proximate the sample cell and downstream of the optics in the branch of the optics between the light source and the cell. A variation in the light beam intensity sensed by the photodiode is used to correspondingly increase or decrease the voltage of the power source for the light source so as to maintain the light beam intensity constant and at a predetermined level. Consequently, variations in the light beam intensity due to fluctuations in the power supply voltage, the age of the light source and the like are prevented from affecting the fluorescent emissions by the particles in the sample being tested.

The detector itself is a photomultiplier, preferably a photomultiplier tube which generates an output charge or signal pulse in response to each photon sensed by the tube. The construction of such photomultiplier tubes is well known. Suffice is to say that the output of the tubes includes noise caused by thermal electrons emitted by the dynodes of the tube and which produce corresponding noise pulses at the output side. The noise pulses have an amplitude significantly lower than the amplitude of the charge pulses caused by the sensed photons. To prevent the noise pulses from affecting the ultimate photon count a discriminator eliminates from the count pulses of an amplitude less than a predetermined minimum, e.g. less than about the amplitude of the noise pulses. The photon pulses are passed to appropriate counting electronics such as cascaded BCD counters.

As a consequence of the foregoing, the ultimate photon count is highly accurate and is typically within a range of one to three percent, which is fully within acceptable limits for FIA.

The present invention further fully automates the placement of samples in the sample cell and their replacement with fresh samples while assuring a complete rinsing of the cell and associated fluid conduits to prevent one sample from affecting the photon count of the next.

In this regard, the present invention contemplates to form a hollow sample cell in a transparent, e.g., quartz housing having a generally square (or rectangular) cross-section with correspondingly perpendicular sides. One side faces and is perpendicular to the incoming light beam and another one faces the photomultiplier and is perpendicular to the fluorescent emissions received thereby. The housing includes a sample inlet connected with the sampler and a sample outlet connected with a sample discharge point, e.g. a container which receives tested samples as waste for subsequent disposal. The sampler is connected to the cell housing inlet via an inert conduit such as flexible polytetrafluoroethylene (Teflon) tubing. The outlet of the cell housing is connected to the discharge point via a readily flexible hose. A sample pump is located between the outlet and the discharge point and preferably comprises a peristaltic pump which conventionally acts on the flexible hose so that the sample is drawn by suction from the sampler into the cell and is not subjected to the potentially damaging mechanical action of a pump. The sample cell and the intake tubing are rinsed before a new sample is drawn into the cell to assure that all remnants of the previous sample are removed before the fresh sample is introduced.

The present invention further appropriately sequences the operation of the pump so that a fresh sample is intermittently drawn into the cell and is stationarily maintained in the cell for the necessary time period to measure its fluorescence, typically about two seconds. Thereafter, the tested sample is withdrawn, the cell is washed with a rinse solution and filled with a fresh sample for measuring its fluorescence. Thus, the entire process is automated and the need for constant supervision of the device by a skilled operator is eliminated.

The sampler of the system of the present invention comprises a holder for supporting a multiplicity of vials or test tubes in an upright position in a row and it includes means for advancing the row in incremental steps so as to present the vials at a vial aspiration station. An aspirator is provided which includes a downwardly open suction tube that can be vertically inserted into and withdrawn from the vial. While in the vial the tube is subjected to a vacuum by the sample tube to withdraw or aspirate the fluid and flow it to the analyzer. In addition to its vertical mobility, the suction tube can be moved in a transverse, generally horizontal direction and a container for a rinsing solution is normally placed proximate the aspiration station and located so that the suction tube can be aligned therewith for immersing the tube in the container after the aspiration of a vial to remove from the tube remnants from the sample in the previously aspirated vial and thereby prevent the cross-contamination of samples. The sample tube draws a sufficient volume of the rinsing solution into the suction tube and hence through associated tubing and the sample cell in the analyzer to purge therefrom the entire previous sample before a new one is aspirated from the next vial.

To thoroughly mix the sample before its withdrawal, a mixer is provided which can be inserted in the vial simultaneously with the suction tube. to accomplish this in spite of the usually very restricted vial diameter (typically no more than 12 mm) the suction tube is fixedly attached to an aspirator arm which also rotatably mounts a mixing tube concentrically about the suction tube. The lower end of the mixing tube is serrated or notched to facilitate the agitation of the solution and its uniform mixing. A drive motor is mounted to the aspirator arm and coupled with the mixing tube via suitable belting or the like to rotate the tube when it is disposed in a vial or in the rinsing solution container.

Preferably, the vial holder comprises a tray that is rotatably mounted and on which the vials are loaded in at least one and preferably two or more circular rows which are concentric with the axis or rotation of the tray. The tray includes a notched index plate which is engaged by a copperating detent biased against the index plate. A vial in each row is aligned with the aspiration station whenever the detent engages a corresponding notch.

The drive for the tray is an intermittent drive that is independent of the positioning index to prevent cumulative positioning errors as would be encountered with gear drive-positioners. Accordingly, it comprises a resilient overdrive which advances the tray so that the detent can engage the next adjacent notch without otherwise affecting the positioning of the vials at the aspiration station.

The aspirator arm is mounted so that it can be pivotally moved about an upright pivot axis whereby the suction tube and the mixer prescribe a circularly arcuate path. The vials at the aspiration station as well as the rinse solution container are positioned along that circular path of the suction tube and mixer so that the latter can be aligned with the former before they are immersed therein. In a preferred embodiment of the invention the rinse solution container is located at one terminal point of the pivotal aspirator arm motion while the vial closest to the axis of rotation of the tray is positioned at the other terminal point of the arm motion. Vials that are in vial rows on the tray radially outward of the innermost row are then located at intermediate points along the circularly arcuate travel path of the suction and mixing tubes. Suitable drive means including locators arrest the pivotal arm motion whenever the tubes are in alignment with the vial or the container in which they are to be immersed next.

A vertically reciprocating rod, the upper end of which mounts the aspirator arm is provided for raising and lowering the arm together with the mixing and suction tubes so as to immerse the tubes in and withdraw them from the vials at the aspirator station or the container.

To eliminate the need for intricate gearing, which is expensive and requires the utmost precision to avoid cumulative positioning errors, the present invention employs individual and independent drives for each of the motions of the tray and the suction and mixing tubes. Thus, there is an independent drive for advancing, i.e. rotating the tray in increments; for pivoting the aspirator arm to position the tubes; for raising and lowering the tubes to insert and withdraw them from the vials and the rinsing solution container; and for activating the mixer. Position sensors provide an electrical signal for indicating the proper positioning of various of the above-described components. In particular, sensors are provided to verify the vertical positioning of the aspirator arm (up and down sensors), the horizontal movement of the aspirator arm (inner row, outer row, and rinse position sensors), and the sequential stepped movement of the turntable (turntable sensor).

An assay procedure according to the present invention requires that a number of say 10 or 12 standards samples be sequentially aspirated and their fluorescence measured, and a dose response curve computed prior to the aspiration and fluorescence measurement of samples having unknown concentration. To this end, the present invention provides a microcomputer system that provides for a given sample (whether a standard sample or a sample to be measured) a proper sequencing of the pump, the counting electronics, and the aspirator motions, and for the overall procedure a proper sequencing of the sampler turntable with appropriate computations being carried out during different points of the cycle.

The microcomputer system includes a primary microprocessor (hereinafter sometimes simply "processor" or "microprocessor") which is interfaced via appropriate latches and buffers on a data bus to system memory, system peripherals, and major system subassemblies. In particular, the primary processor communicates with the counting electronics, appropriate sequencing electronics controlling the sampler, and a separate arithmetic processor. Additionally, the processor communicates with keyboard switches, electronics controlling a display and a keyboard, and an interface that permits data transfer to a remote computer.

The sampler sequencing electronics itself is preferably microcomputerized so that the primary processor is able to control the sampler relatively simply without having to assume responsibility for the particular details of the sampler operation. In particular, the sequencing electronics includes a microprocessor that receives and responds to the electrical signals from the sampler's position sensors and provides electronic signals at appropriate intervals for actuating the sampler's motors.

The overall operation of the present invention may now be briefly summarized as follows, first with respect to the sampler sequencing, then with respect to the fluorescence measurement, and finally with respect to the data reduction.

The aspirator has a home or rest position at which the suction tube is aligned with an immersed end in the rinsing solution container. To commence sampling, the tray drive is energized to present the first vial (or vials if there are multiple vial rows on the tray) at the aspirator station. The exact positioning is performed by the index plate and the cooperating detent. Upon the proper positioning or, to save time, even before that the aspirator arm is raised to withdraw the suction and mixing tubes from the rinsing soltuion and to clear the upper ends of the container and the vials. Thereupon, the aspirator arm is pivotally moved until the tubes are aligned with the vial at the aspirator station in one of the rows, say the radially outermost row. Upon alignment, the aspirator arm is lowered until the lower end of the rotating mixer tube is proximate to but spaced from the bottom of the vial. The mixing tube is now rotated at a relatively high rate to intimately mix the liquid in the tube and to thereby uniformly disperse all particles throughout the liquid.

After completion of the mixing step, typically after about four seconds, mixing ceases and the liquid is aspirated from the vial by suction through the suction tube by energizing the sample pump. After a sufficient amount of sample has been withdrawn to fill the sample cell in the analyzer, pumping ceases and the aspirator arm is again raised to clear the upper end of the vials. The arm is now pivoted to return the tubes to the rinsing container where they are immersed, the mixing tube is rotated. After the sample in the cell has been analyzed the sample pump is actuated and rinsing solution is flowed through the aspirator, the pump and associated tubing into the sample cell to purge the previous sample and thus prevent the contamination of the next sample.

Thereafter, the mixing and suction tubes are repositioned as above described to align them with a vial in the next, e.g. the radially inward row without again activating the tray advancing drive. The above-summarized mixing, withdrawing and rinsing steps are repeated. After the vial in the last vial row has been aspirated, and usually while the tubes are being rinsed, the tray is advanced by one increment to position the next set of vials at the aspirator station.

Fluorescence information regarding a particular sample within the sample cell is accomplished by a counting sequence wherein the primary processor initially clears the counting electronics and then enables the counters for a period determined by a software loop of a fixed number of machine cycles, the machine cycle duration being precisely fixed by the processor's crystal controlled clock. counting is monitored by the processor, and a multi-digit count is determined and stored in system memory for subsequent processing.

As described above, prior to counting the fluorescence of actual samples, the fluorescence of a number of say 10 or 12 standard samples is measured and the microprocessor computes a dose-response curve for one or more and preferably for four data reduction techniques, to wit a linear interpolation, a logit-log, hyperbolic and reciprocal program and retains in memory the standard curve parameters for the reduction technique that gives the best regression coefficient. For thyroxine or triiodothyonine that coefficient is typically in excess of 0.990 for the logit function. With the dose-response curve computed, the fluorescence of each of the samples is measured and the concentration of antigen in the sample is computed and printed out. This is accomplished on a continuing basis until all samples in a given set have been measured.

From the foregoing, it will be apparent that the present invention provides an entirely automated system for mixing clinical samples while they are in their vials, for sequentially transferring large numbers of samples to the sample cell, and for independently analyzing each sample while assuring that all remnants of each sample are rinsed before the next sample is introduced into the cell to prevent a sample cross-contamination and a possible reduction in the accuracy of the test. The test itself is accurate to within 5% or less. The automated handling of the samples, their automated analysis, and the recordation of the test results for each sample greatly simplify and speed up the testing procedure while freeing highly trained technicians for other than repetitive manual tasks. This not only results in an improved test accuracy, but also reduces the cost of the tests and thus aids in lowering the otherwise ever increasing cost of clinical tests.

BRIEF DESCRIPTION OF THE DRAWINGS

FIG. 1 is a diagram which schematically illustrates the overall arrangement of the system of the present invention;

FIG. 2 is a more detailed, schematic illustration of the analyzer which forms part of the present invention;

FIG. 3 is a schematic of the stabilization circuit for the light source employed by the analyzer;

FIG. 4 is a schematic of the discriminating circuit of the present invention employed in the analyzer;

FIGS. 5A-C are diagrams which illustrate the conditioning of the output signals of a photomultiplier by the circuit shown in FIG. 4;

FIG. 6 is a schematic of the photon pulse counting circuit of the present invention;

FIG. 8 is a plan view of the keyboard, illustrating the various key functions;

FIG. 9 is a perspective, overall view of a sampler constructed in accordance with the present invention for automatically mixing samples in and withdrawing them from a multiplicity of vials;

FIG. 10 is a perspective view similar to FIG. 9 but with all exterior covers removed so as to illustrate the drives employed by the sampler of the invention;

FIG. 11 is a perspective, enlarged, fragmentary view of an aspirator arm constructed in accordance with the invention and employed on the sampler illustrated in FIG. 9;

FIG. 12 is a fragmentary, side elevation view, in section of the aspirator arm and is taken on line 12—12 of FIG. 11;

FIG. 13 is a fragmentary end view of the suction tube and the mixer employed by the aspirator of the present invention and is taken on line 13—13 of FIG. 12;

FIG. 14 is a fragmentary, perspective elevation with parts broken away, and illustrates the drive for raising and lowering the aspirator shown in FIG. 11;

FIG. 15 is a fragmentary plan view of the sampler shown in FIG. 9 with parts broken away and with the cover omitted;

FIG. 16 is a plan view similar to FIG. 15 but illustrates components of the sampler in differing positions, with some of the positions being superimposed and shown in phantom lines; and FIG. 17 is a simplified circuit schematic of the sampler control circuitry.

DESCRIPTION OF THE PREFERRED EMBODIMENTS

Figure 7:
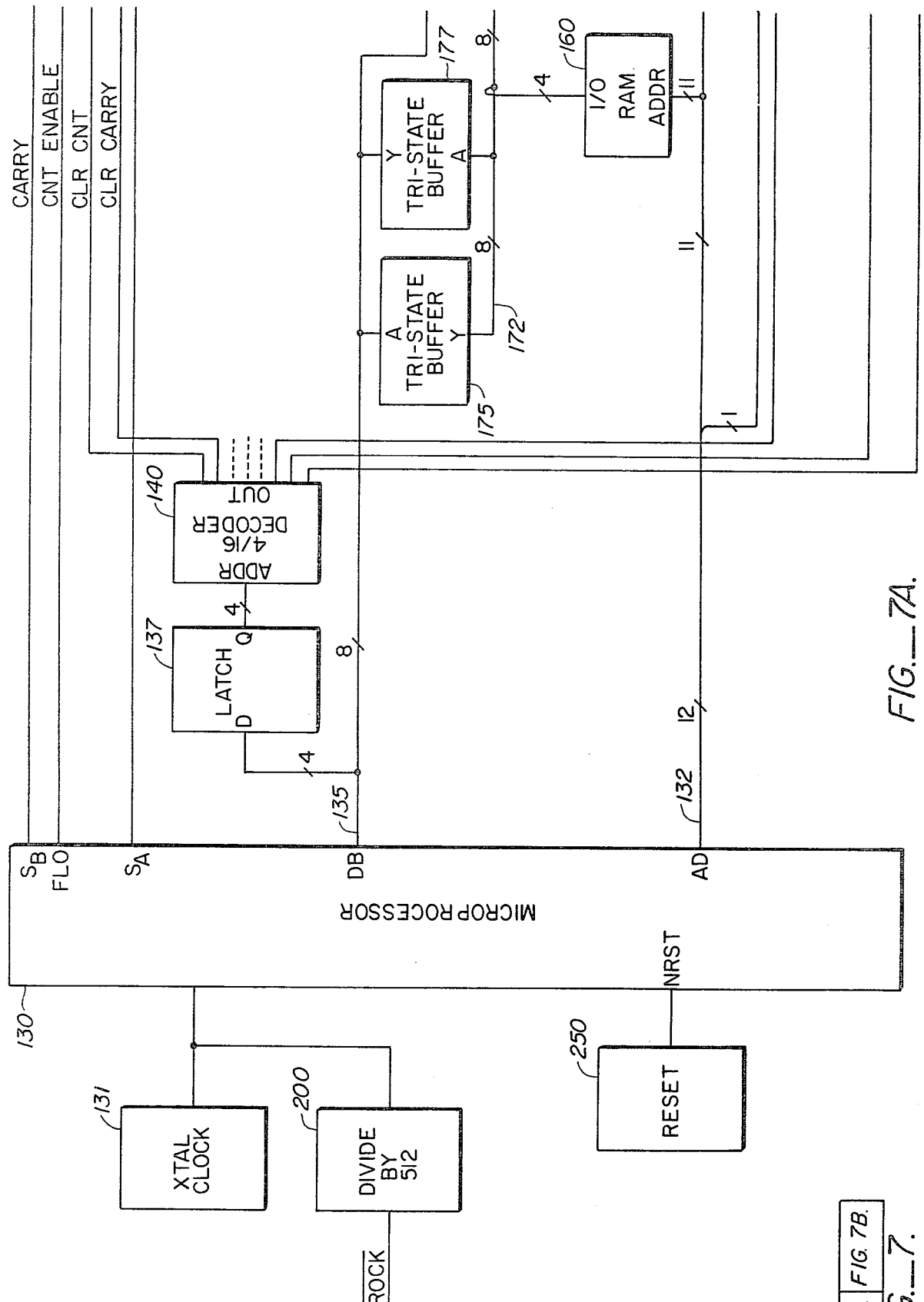
FIGS. 7A-B, taken together, form a simplified circuit schematic of the microcomputer system of the present invention.

Referring first to FIGS. 1 and 2, an automated system 2 constructed in accordance with the present invention for performing fluorescent immunoassays and in particular for quantitating relatively small amounts of a clinically significant composition such as thyroxine, for example, comprises a sample holding cell 4 which forms part of a flow system 6; a sampler 7 for sequentially retrieving large numbers of samples; optics 8 including a first optical branch 10 for subjecting the sample in the cell to a beam of light and a second optical branch 12 for collecting fluorescent emissions generated by fluorescing particles in the sample when excited by the beam; a photon detector 14 including photon counting electronics 16 which receives the fluorescent emissions from the sample in the cell; and system electronics 18 for appropriately analyzing the photon count for each sample as is more fully discussed below and for sequencing the various operations performed by the present invention.

System electronics 18 includes a microcomputer 20, a display controller 21 for interfacing to a visual display panel 22, a printer controller 23 for interfacing to a printer 24, a keyboard 26 for inputting various data and commands, and sequencing control electronics 28 controlled by microcomputer 20 for initiating and terminating various functions of sampler 7. To facilitate the understanding of the invention, the subfunctions and subsystems of the apparatus will be individually discussed before the overall operation of the apparatus is described in detail.

The sample flow system 6 comprises as its central part a flow housing 30 constructed of an optically pure, transparent material such as quartz and which has a square cross-section as is best seen in FIG. 2 to form four mutually perpendicular sides including a first side 32 which is perpendicular to the optical axis 34 of the first optical branch 12 and a second side 36 which is perpendicular to the optical axis 38 of the second optical branch 12 (and which is also perpendicular to the first optical axis 34). The housing defines sample cell 4 which also has square cross-sections and which has flat interior walls that are parallel to the exterior sides of the housing. An inlet 40 of the housing is connected to a length of preferably flexible intake tubing 44 constructed of a chemically inert material such as Teflon. The other end of the intake tubing fluidly communicates with a sampler 7.

The outlet 42 of the cell housing communicates with a point of discharge 54 (which may comprise a waste solution bottle or container, not separately shown) via a discharge hose 56 made of a readily and repeatably compressible material, such as Tygon tubing. Since only waste materials flow through the discharge hose, it need not be constructed of inert material.

A sample pump 58 is placed downstream of the sample housing 30 and draws a sample or rinsing solution from appropriate vials (not shown in FIGS. 1 and 2) on sampler 7 into the sample cell 4 by suction. Direct contact between the pump and the fresh sample and potential mechanical damage to the sample constituents are thereby prevented. Preferably, the pump comprises a conventional peristaltic pump which engages the outer surface of the discharge hose 56. Pump 58 is controlled by computer 20 through appropriate pump driving circuitry 59 as is further described below.

The sample housing 30 is disposed in a generally L-shaped, optical chamber 60 at about the intersection of the perpendicular chamber legs 62 and 64, so that the center of the flow cell 4 is at the intersection of the perpendicular optical axes 34, 38 which also positions housing sides 32, 36 perpendicular to the respective optical axes.

The other end of the first optical branch 10 is defined by a light source 66. Preferably, the light source comprises a 50 W tunsten halogen lamp provided with a parabolic reflector 68. In the optical train between the light source and the sample cell are a heat absorbing filter 70, a condensing lens 72 and a narrow band pass or interference filter 74. For instances in which the fluorescent is fluorescein (which has an excitation wavelength of 490 nanometer (nm) and an emission wavelength of 520 nm) the band pass filter 74 comprises a 490 nm narrow branch pass inerference filter.

The second optical branch 12 terminates in a photomultiplier tube 76 (PMT) disposed in the optical chamber leg 64 opposite the second sample housing side 36. Disposed between the sample housing and the PMT are a cutoff filter 78 made of low fluorescence glass to block the excitation wavelength, a collecting lens 80 and a narrow band pass filter 82. For the above-discussed fluorescent the cutoff filter is a 515 nm cutoff filter to prevent scattered excitation light from reaching the PMT while the band pass filter is a 520 nm narrow band pass interference filter to isolate the emission wavelength and limit the light reaching the PMT to the emission wavelength.

To eliminate stray light and light reflections which can directly or indirectly adversely affect the photon count by the PMT 76, the interior of housing 60 is black. Further, a light trap 65 is provided in the form of a well or depression formed in the housing wall at the extension of the first optical axis 34. The light trap prevents light which passes through cell housing 34 from being reflected back into the cell (and thereby causing secondary fluorescent emissions) and from being reflected into the second optical branch 12 where it could affect the photon count by the PMT.

As should be apparent, upon energizing light source 66 light of the excitation wavelength, e.g. 490 nm is focused onto the sample in cell 4 and stimulates the fluorescing particles in the samples to generate fluorescent emissions of a predetermined wavelength, e.g. 520 nm. The fluorescent emissions propagate in all directions equally and those propagating along the second optical axis 36 are focused onto the cathode (not separately shown) of the PMT 76. In the preferred embodiment, the PMT is a nine-stage, side-on type PMT specifically adapted for photon counting. It operates with a cascade effect in which an electron emitted by the photocathode due to an impinging photon is accelerated to the first dynode (not separately shown) of the PMT by a high voltage bias where it generates a number of secondary electrons. The number of secondary electrons is a function of the bias voltage and the dynode material and structure. The secondary electrons are then accelerated to the second dynode where each generates a number of additional secondary electrons. The process continues down the dynode chain to the anode of the PMT, thereby producing a large current amplification.

Quantitatively, the fluorescent emissions of the excited sample in cell 4 are a function of the intensity of the excitation light beam from light source 66 and the concentration of fluorescent particles in the sample or, since the cell volume is fixed, the total number of fluorescent particles in the sample cell. Thus, any fluctuation in the intensity of the excitation light beam would result in a corresponding change in the intensity of the fluorescent emissions and cause an error which is a function of the intensity change in the excitation beam. Since the overall accuracy of the system of the present invention should not deviate by more than three percent variations in the excitation beam intensity in excess of one percent from normal are to be avoided. Light beam intensity changes in excess of one percent are frequently encountered because of fluctuations in the line voltage, intensity changes due to the age of the light source and the like. To prevent these from affecting the charge pulse count from the PMT 76, the present invention provides the light source stabilization circuit 84 illustrated in FIG. 3.

Referring now to FIGS. 2 and 3, a silicon photodiode 86 is positioned in the optical branch 10 immediately adjacent flow housing 30, that is optically downstream of heat absorbing filter 70, condensing lens 72 and band pass filter 74, so that light focused onto the sample in cell 4 is also sensed by the photodiode. The photodiode operates in the photoconductive mode and its output is amplified in a preamplifier 88, the output of which is compared to a preset reference voltage $V_{ref}$ in a comparator 90. The reference voltage may be obtained from a precision voltage divider comprising a resistor and a trimmer potentiometer (not separately shown) and, once set, it is typically not changed. The comparator output is then used to modulate a triac 92 for the light source to maintain the intensity of its light beam constant.

In a preferred embodiment of the invention, the comparator senses the error voltage and forms as an output either $+10$ V or $-10$ V, depending on the error voltage, which is sent to an integrator 94. The integrator ramps in the appropriate direction to adjust a triac switching reference voltage. The switching reference is inverted to obtain both a positive and a negative switching reference. This bipolar reference is applied to a pair of triac drivers 96 along with the attenuated 24 V A.C. output of transformer 98. During each half cycle of the A.C. wave form, the triac is off until the A.C. voltage exceeds the switching reference level. When the A.C. voltage swings above the reference level, the triac is gated on and conducts until the A.C. voltage falls back below the reference. In this manner, the duty cycle of the light source A.C. power input is modulated to maintain its output constant.

With a constant excitation beam the fluorescent emissions for a given sample in cell 4 remain likewise constant. Referring now to FIGS. 2, 4 and 5A-C, to maximize the sensitivity of detector 14, the detector operates in a photon counting mode in which an individual charge or signal pulse is produced by the PMT 76 for each photon which reaches the PMT's photocathode (not separately shown). The PMT operates in this mode for light levels of between about $10^{-11}$ to $10^{-13}$ W.

Thermal electrons are also emitted by the dynodes and they produce noise pulses at the anode which constitute an undesirable noise component which can adversely affect the signal pulse count. The noise pulses have a substantially lesser amplitude than the photon generated signal pulses and to eliminate them, a discriminator 100 precedes the photon counting electronics 16. As is illustrated in FIG. 5A, the noise component of the signal is relatively large at low voltages and relatively small at higher voltages. To eliminate most the noise pulses, a reference voltage $V_{ref}$ is chosen at a level at which the signal count S is relatively high and the noise count N is relatively low as is indicated in FIG. 5A.

Both noise and signal pulses are amplified in an amplifier 102 and the amplifier output is fed to a comparator 104 which acts as an amplitude discriminator and receives as its second input a preset reference signal from an appropriate source 106. The comparator eliminates all pulses having an amplitude less than $V_{ref}$ as is indicated in FIG. 5B and thus yields an output signal which essentially comprises only signal pulses SP while all noise pulses NP (except for one illustrated in FIG. 5B and 5C) have been eliminated.

The reference voltage $V_{ref}$ of the comparator 104 is typically preset to provide the optimum signal to noise ratio for the PMT-amplifier-comparator combination by blocking the majority of noise pulses while passing most of the charge pulses. If desired, it can also be continually adjusted by appropriately selecting the optimal $V_{ref}$ level at which the signal pulse to noise pulse is greatest. The output from the comparator, namely the signal pulses are fed to the counting electronics 16.

Referring to FIG. 6, in a preferred embodiment of the invention, counting electronics 16 comprises four cascaded four-bit BCD counters 108, 110, 112, and 114. Each counter has a clock input, designated CLK, a carry output, designated C/O, and a 4-bit data output, designated Q. The output from comparator 104 communicates through a buffer to the input of counter 108; the carry output of counter 108 comminucates through a buffer to the input of counter 110; the carry output of counter 110 communicates through a buffer to the input of counter 112; the carry output of counter 112 communicates through a buffer to the input of counter 114; and the carry output of counter 114 communicates to the clock input of a "carry" flip-flop 120. Flip-flop 120 has a clear input, designated CLR which may receive signals from microcomputer 20 on a line 121. The output of flip-flop 120, designated Q, communicates to microcomputer 120 via a line 122. The outputs of counters 108 and 112 are communicated to the inputs of an 8-to-4 multiplexer 124. Similarly the outputs of counters 110 and 114 are communicated to the inputs of an 8-to-4 multiplexer 125. The 4-bit outputs of multiplexers 124 and 125 together form an 8-bit data line 126. Multiplexers 124 and 125 have respective select inputs, designated SEL, which are tied together and receive signals on a line 127. Each counter also has an enable input, designated EN, to enable counting, and a clear input, designated CLR, to zero the counter contents. The enable inputs are tied together and receive signals from microcomputer 20 on a line 128. The clear inputs are tied together and receive signals on a line 129.

Before discussing the systems electronics 18 of the invention, the construction and operation of sampler 7 will be described in detail. Referring now to FIG. 9, in a preferred embodiment of the invention the sampler 7 comprises a case 304, a holder 306 mounted to the case for rotation about an upright axis 308 and holding a multiplicity of clinical test tubes or vials 310 in an upright position so that their open ends 312 face upwardly, and an aspirator 313 mounted to the case for withdrawing liquid samples from the vials. The aspirator includes a generally horizontal aspirator arm 314 that is pivotal about a vertical axis 316 for pivoting an aspirator assembly 318 about axis 316 to align it with vials at an aspiration station 320 or with a rinse container 322 holding a volume of a rinsing solution 324.

In a presently preferred embodiment the rinse container is entirely separate of the case 304 and the vial holder 306 and has a flat bottom so that it can stand on the case. This allows a quick removal of the container for cleaning the sampler and the like. By giving the container a relatively larger inner diameter, it is readily repositioned on the case without requiring a precise alignment with the aspiration station since the larger inner diameter compensate for slight alignment errors.

The vial holder comprises a tray defined by a pair of vertically spaced apart discs 326, 328 interconnected by a hub (not separately shown) and fixedly secured to an upright shaft 330 for rotation therewith about upright axis 308. The discs include vertically aligned sets of upper and lower holes 332, 333 which are arranged in an inner and an outer circular row 334, 336 and which are dimensioned so that the vials can be slidably inserted through the upper holes 332 and are engaged and centered by but cannot pass through the lower holes 333 to thereby mount the vials in an upright position. By intermittently rotatably advancing shaft 330 and the discs, the vials are sequentially presented at the aspiration station.

In operation, the vials are filled with a given volume of sample liquid, say 5 ml for 10 mm diameter vials and upon the alignment of one or more vials with the aspiration station, the aspirator arm 314 is pivoted to align the aspirator assembly 318 with a vial. The assembly is thereafter lowered as is discussed in more detail below to immerse it in the sample in the vial, the sample is mixed to form a uniform suspension, and thereafter it is withdrawn by energizing a sample pump 58 which forms a vacuum in the assembly and draws the sample from the vial via tubing 44 to sample cell 4 where the sample is analyzed and tested in the manner described elsewhere.

The aspirator 318 is then retracted from the vial and the aspirator arm 314 is pivoted to align the assembly with rinse container 322. The assembly is immersed in the solution and in a preferred embodiment of the invention pump 58 is energized after the previous sample in cell 4 has been tested to draw a volume of rinse solution through the assembly, tubing 44 and the sample cell. As the rinsing solution is drawn in the previous sample is purged from the cell and the associated tubing and hence discharged via a discharge conduit 56.

Upon the completion of the rinsing step the aspirator assembly 318 is again withdrawn from rinse container 322 and is aligned with the next vial at the aspiration station. The assembly is immersed in the sample in the next vial and pump 58 is energized to draw a fresh sample into the analyzer while the rinsing solution previously flowed into the analyzer is purged therefrom and discharged via conduit 56.

These steps are repeated until all vials on the holder have been aspirated. Thereupon, the vials may be replaced or the holder as a whole may be lifted from case 304 and replaced with another holder filled with vials holding liquid samples to be tested.

Referring now to FIGS. 9-14, the aspirator assembly 318 has an elongated, inner suction tube 346 which is immovably attached with a set screw 350 or the like to a bracket 348 carried by the aspirator arm 314. A mixing tube 352 is concentrically disposed about the suction tube and is carried by a hub 354 rotatably mounted to the aspirator arm so that the rotation of the hub results in a corresponding rotation of the mixing tube.

An open lower end 356 of the mixing tube protrudes past the lower end of the suction tube. The lower end of the mixing tube includes a pair of downwardly opening grooves 362 which, when immersed in liquid and when the mixing tube is rotated, significantly enhance the agitation and mixing of the surrounding liquid. The entire assembly has an outermost diameter less than the inner diameter of the vial so that the assembly can be inserted in and retrieved from the vial in a vertical direction while ensuring that the mixing tube can freely rotate. When the diameter of aspirator assembly is of no concern a flexible sleeve (not shown) may be placed over the outer diameter of the mixing tube. In such an event the sleeve protrudes below the lower end 356 of the mixing tube and the grooves 362 are formed in the sleeve.

The aspirator arm 314 is defined by a channel 364 the forward, i.e. righthand end of which as seen in FIG. 12 mounts the aspirator assembly 318. An electric mixing motor 366 for rotating mixing tube 352 is mounted to the channel adjacent an aft end thereof and includes a grooved pulley 368 over which a drive belt 370 such as an endless resilient rubber ring is slung. The drive belt also engages a corresponding groove in hub 354 so that the motor can rotate the mixing tube 352 carried thereon about the upright axis defined by suction tube 346. The arm further includes a vertically oriented, downwardly extending mounting sleeve 372.

A vertically reciprocable rod or post 374 defines pivot axis 316, extends into sleeve 372 and through a guide tube 375 that projects from case 304 into the interior of the case where it is carried by a movable frame 376 disposed within the case. The rod has an axially extending flat face which carries a gear rack 390 for purposes further described below. The interior of sleeve 373 has a corresponding radially inwardly projecting protrusion (not shown) for engaging the flat face of the rod to prevent relative rotational movements between the aspirator 313 and the rod while permitting the ready removal of the aspirator from the rod by slipping the former in a vertical direction off the latter.

The movable frame has a generally U-shaped configuration with upper and lower flanges 378, 380 disposed proximate a housing 382 and a base 384, respectively, of case 304. The lower end of the guidance tube is affixed to the upper flange 378 and protrudes through a hole formed in the case housing. The lower flange 380 of the frame receives an aligned shaft (not separately shown) which protrudes through a correspondingly positioned hole in the base 384, so that the frame 376 and therewith guide tube 375 can be pivoted about upright axis 316 for purposes further described below.

A pair of spaced apart, parallel and vertical guide posts 386 are affixed to the upper and lower flanges 378, 380 of the frame and they straddle guide tube 375. A yoke 388 has holes formed to slidably engage the guide posts so that the yoke can move vertically along the posts from a lower position 388A to an upper position 388B, both of which are shown in phantom lines in FIG. 14.

The lower end of upright rod 374 is affixed to yoke 388 and its gear rack 390 meshes with a pinion gear 392 driven by a reversible electric motor 394 attached to the back side of frame web 396 facing away from the vertical guide posts.

Upper and lower position transducers such as optical sensors 398, 400 are attached to the frame, e.g. to frame web 396 and they cooperate with an indicator 402 attached to yoke 388 so as to generate upper and lower position signals when the yoke is in its raised or lowered positions. Signals from the sensors are used to de-energize motor 394 when the yoke and therewith upright rod 374 reach these positions.

Preferably, motor 394 is a load reversing motor, i.e. a motor which reverses its direction of rotation upon encountering a predetermined torque on its shaft to prevent damage to the motor or the associated gearing should either of the optical sensors fail or if an excessive load is applied to the upright rod due to an interference between the aspirator 313 and any of the vials 310, rinse container 322 or other hardware.

Referring now to FIGS. 10, 11 and 14–16, movable frame 376 and therewith upright rod 374 are also pivotable about axis 316. The pivotable frame motion is imparted to the aspirator arm 314 by virtue of the engagement of the upper end of post 374 with mounting sleeve 372.

Pivotable motion is imparted to the frame 376 by a crank arm 404, the respective ends of which are pivotally attached to lower flange 380 of the movable frame and to a crank pin 406 eccentrically mounted to a crank wheel 408 disposed between base 384 and a platform 410 vertically spaced therefrom. An upright shaft 412 to which the crank wheel is mounted protrudes through the platform and is driven by a motor 414 mounted to the underside of housing 382 with spaced apart mounting bolts 416.

An indicator arm 418 rotates with shaft 412 and is positioned to interrupt three optical sensors 420, 422 and 424 during one full rotation of the crank wheel to generate three position signals. The three signals are used to deenergize motor 414 to terminate its rotation when the movable frame 376 and therewith aspirator assembly 318 are at predetermined locations as is further discussed below. A tension spring 426 biases the movable frame in a clockwise direction to take up play and prevent backlash in the pivoting mechanism.

When motor 414 is energized it rotates shaft 412 via gearing 428 and therewith crank wheel 408 and indicator arm 418. Rotation of the crank wheel is transmitted to the frame via crank arm 404 to pivot the frame between terminal positions 376A (shown in FIG. 16) and 376B (shown in FIG. 15). The pivotal frame movement is duplicated by aspirator 313 and places the aspirator arm 314 in terminal positions 314A (FIG. 16) and 314B (FIG. 15). The two terminal positions coincide with the alignment of indicator arm 418 with optical sensors 420 and 424, respectively. The aspirator arm 314, movable frame 376, crank arm 404 and crank wheel 408 are sized so that when the frame is in position 376A (FIG. 16) the aspirator arm vertically aligns the aspirator assembly 318 with a vial at position 310A (FIG. 16) in the inner vial row 334 at aspiration station 320.

It should be noted that the aspiration station is defined by a circularly arcuate line the origin of which is vertical axis 316. The line has a radius equal to the distance between this vertical axis and the axis of the aspirator assembly so that the aspirator assembly can be vertically aligned with any point on this line.

The second terminal point 376B of the pivotal frame 376 is chosen so that it vertically aligns the aspirator assembly with rinse container 322 when the aspirator arm is at position 314B (FIG. 15). In that position, indicator 418 is aligned with optical sensor 424 to generate a position signal which indicates the alignment of the mixing-withdrawal assembly with the rinse container.

A third, intermediate position 376C of the movable frame (FIG. 16) is determined by optical sensor 422. When the indicator 418 is aligned with sensor 422 aspirator arm 314 is at position 314C (FIG. 16) and the aspirator assembly is aligned with a vial at position 310C in outer vial row 336 at aspiration station 320.

From the foregoing, it will be apparent that the relative position of the vial receiving holes 333, 334 in discs 326, 328 should be carefully chosen to minimize motion and indexing of the vial holder 306 as is further discussed below. Accordingly, the vial holes are arranged so that two holes are simultaneously aligned with aspiration station 320 or, expressed in other words, so that two holes, one in each of rows 334 and 336 lie on a circularly arcuate line, the origin of which is vertical axis 316 and the radius of which equals the distance between this axis and the center of the aspirator assembly. When so positioned, two vials, one in each row can be aspirated before the vial holder 306 must be advanced to present the next set of two vials at the aspiration station.

Referring now to FIGS. 9–16, the manner in which the aspirator assembly 318 is moved to sequentially aspirate the vials at the mixing station should be apparent. To briefly summarize, movable frame 386 has a home position 376A at which the aspirator assembly is aligned with rinse container 322. To initiate the aspiration of liquid samples from vials at the aspiration station 320, motor 394 raises upright rod 374 and therewith aspirator arm 314 and aspirator assembly 318 until the lower end of mixing sleeve 360 clears the upper edges of both the rinse container and the vials. At that point motor 394 is de-energized.

Motor 414 is now activated to rotate crank wheel 408 until indicator 418 interrupts optical sensor 420 and the frame is at position 376A ((FIG. 16) to vertically align the aspirator assembly with the vial at position 310A on inner vial row 334. The interruption of sensor 420 de-energizes motor 414 and thereby arrests the pivotal motion of frame 376. Vertical position motor 394 now lowers rod 374 and therewith the aspirator assembly until the lower end of mixing sleeve 360 is proximate but slightly spaced above the bottom of the vial. This position is determined when indicator 402 interrupts the lower optical sensor 400 mounted to frame 376.

Mixing motor 366 is now energized to rotate mixing tube 352 at a relatively high rate, say 4500 rpm for the necessary time to uniformly disperse all particles in the liquid sample and form a homogenous suspension. For dissolving centrifuged pellets and suspending them in the liquid a mixing time of four seconds is normally sufficient. Upon completion of the mixing pump 58 is activated to withdraw the desired sample volume by suction through suction tube 346 and flow it to sample cell 4. The pump is de-energized as soon as the necessary volume has been withdrawn from the vial.

While the sample is being analyzed, vertical position motor 394 raises the aspirator assembly 318 end motor 414 rotates crank wheel 408 in a counterclockwise direction (as seen in FIG. 16) until indicator arm 418 interrupts sensor 424. It will be noted that the indicator arm passes through optical sensor 422 and suitable logic is provided to override the position signal generated by sensor 422 and to continue the operation of motor 414 until the indicator is at sensor 424. The aspirator assembly is now lowered to immerse it in the rinsing solution in container 322.

After completion of the analysis of the previous sample, pump 58 draws rinsing solution by suction from container 322 into tubing 44 and hence sample cell 4 to purge the previous sample and at the same time thoroughly rinse all components that came into contact with it. A cross-contamination of the next sample is thereby prevented.

As rinsing solution is withdrawn from the container, it is refurbished with fresh rinsing solution from a reservoir such as a bottle 430 fluidly connected with the container via tubing 432 and an intake pipe 434 at the bottom of the container so that the rinsing solution level in the container corresponds to the solution level in the bottle. To facilitate an adjustment of that level, particularly as solution is drained from the bottle and/or replenished therein, the bottle is preferably mounted to a vertically adjustable table (not shown).

Returning to the operation of aspirator assembly 318, it is preferred that mixing motor 366 be energized during the rinsing step to facilitate the rinsing of all remnants of the earlier sample. Upon completion of the rinsing step pump 58 is de-energized and the vertical position motor 394 returns the aspirator assembly into its raised position. Thereupon motor 414 pivots frame 376 into its invermediate position 376C until indicator arm 418 interrupts opitical sensor 422. Aspirator arm is at intermediate position 314C and aspirator assembly 318 is aligned with the vial at position 310C in outer row 336. The position signal generated by optical sensor 420 as the indicator arm passes it is suppressed so that the motor remains energized until the indicator arm reaches sensor 422.

The aspirator assembly is now lowered, and the sample in tube 310C is mixed and withdrawn. Thereafter, the aspirator assembly is returned to rinse container 322 and this sample is also purged from all conduits and the analyzer in the manner described above.

With the aspiration of the vial at 310C the samples in all vials at the aspiration station 320 have been tested. Vial holder 306 is now advanced to present the next set of two vials at the station. This is accomplished by means of a tray advancing drive 436 and a tray index 438 best illustrated in FIGS. 10, 15 and 16.

To facilitate the illustration, housing 382 is not shown in FIGS. 15 and 16. However, the vial holder disc 326 is superimposed over the illustrations in FIGS. 15 and 16 so as to pictorially show the interrelationship between the vial positions 310A and 310C at the aspiration station 320 and the vial holder drive and index.

Referring now to FIGS. 10, 15 and 16, the tray index 438 is defined by a circular index plate 440, the periphery of which is scalloped and defines a number of preferably circularly concave index notches 442 which equal in number the number of vial holes in row 334. For a two-row disc, the number of notches equals the total number of vial positions on the disc divided by the number of vial rows or, in the illustrated instance, divided by two. A detent wheel 444 such as a roller bearing is mounted to the upwardly facing side of a plate 446 disposed beneath the index plate and pivotally mounted to an upright post 448 extending from the base 384 to the case housing (not shown in FIGS. 10, 15 and 16). One end of a tension spring 450 is anchored in plate 446 and biases it in a counterclockwise direction as is viewed in FIGS. 15 and 16. The spring thereby biases the convex periphery of the detent wheel 444 towards the index plate 440 and nests the index wheel in a notch. If the two are misaligned, the force from the spring rotatably moves the index plate until the detent wheel fully nests in the notch.

The index plate is affixed to shaft 330 mounting vial holder 306 so that it rotates therewith an it is oriented so that when the detent wheel nests in an index notch 442 a corresponding set of two vial holes in the inner and outer vial rows 334, 336 is at positions 310A and 310C and aligned with aspiration station 320. The tray index 438 permits the rotation of both the vial holder 306 and the index plate 440 by correspondingly pivoting the detent plate 446 about post 448. However, the detent wheel will always come to rest in an index notch and a pair of vial holes will, therefore, always be aligned with the aspiration station.

The tray advancing drive 436 comprises a tray drive motor 452 which includes gearing 454 and which is mounted to the underside of a mounting plate 456 that is pivotable about a post 458 extending between base 384 and housing 382 (not shown in FIGS. 10, 15 and 16). One end of tension spring 450 engages the mounting plate and biases it in a counterclockwise direction, as seen in FIGS. 15 and 16. A stop 460 in the form of another post extending between the base and the housing limits the extent to which the tension spring can pivot the mounting plate.

The tray drive motor 452 drives a crank wheel 462 disposed on the upwardly facing side of the mounting plate and fitted with an eccentrically mounted roller bearing 464 which forms a drive pin for the disc plate 440. The crank wheel and the drive pin are positioned so that when the wheel is rotated through one full revolution, the drive pin engages one of the index plate notches 442 and advances it a sufficient distance so that detent wheel 444 engages the next index notch 442. Typically, the drive pin will advance the index plate by more than one-half the spacing between two adjoining index notches 442 and less than one and a half such spaces to prevent an advance of the index plate 440 by more than one notch.

As the crank wheel and the drive pin are rotated, preferably in a clockwise direction as indicated by the arrow in FIG. 15 and the pin engages an index notch 442, mounting plate 456 is pivoted in a clockwise direction against the force exerted by tension spring 450 to assure a firm engagement of the index notch by the drive pin while avoiding the need for precise dimensional alignments between the drive pin and the index wheel which would otherwise be necessary. Stop 460 prevents a continuous engagement of the drive pin with the index notches, which could result in an overtravel of the index plate, by limiting the extent to which the mounting plate 456 and therewith the drive pin can pivot towards the index plate so that through part of a full rotation of crank wheel 462 the drive pin is disengaged from the index plate.

The pivotal motion of the mounting plate when the crank wheel 462 goes through one full revolution is utilized to de-energize the tray drive motor 452. For this purpose, an optical sensor 466 is mounted to platform 410 and an elongated index arm 468 is affixed to mounting plate 456 and dimensioned so that a pointer 470 of the index arm is normally clear of optical sensor 466 but interrupts it when the mounting plate pivots due to the rotating motion of the drive pin. The resulting signal is used to de-energize the drive motor. Since the signal is generated while the drive pin engages a notch, the de-energization of motor 452 is sufficiently delayed to permit the motor to rotate the crank wheel 462 until the wheel has completed one full revolution and has returned the drive pin to its home position, for example, the position illustrated in FIG. 15. A separate optical detector 469 (shown only in FIG. 17) is used to define a predetermined first position.

Turning now to the overall operation of the sampler 7 and referring to FIGS. 9–16, holder 306 is initially loaded by placing sample holding vials 310 in the corresponding vial holes 332, 333 in discs 326, 328 of the holder. At this point, two vials will be at vial positions 310A, 310C in alignment with aspiration station 320 while aspirator assembly 318 is at aspirator arm position 314B and immersed in rinse container 322. For purposes more thoroughly discussed below, some, say the first 10 vials, represent "standard samples" while the remainder of the vials hold test samples.

Functionally, sampler 7 operates as follows. Vertical position motor 394 is forst energized to raise the aspirator assembly 18 until a signal from upper sensor 398 on movable frame 376 indicates that the assembly is in its raised position. Motor 394 is now de-energized and motor 414 is energized to pivot aspirator arm 314 until the aspirator assembly is aligned with the vial at position 310A. The arrival of the aspirator assembly at that location is sensed by optical sensor 420 motor 414 is de-energized and vertical position motor 394 is activated to lower the aspirator assembly. When the assembly is in its lowered position the lower optical sensor 400 on movable frame 376 generates a corresponding signal and position motor 394 is de-energized. Motor 366 now rotates mixing sleeve 360 for the required time period after which the mixing motor is de-energized. Pump 58 can now withdraw the desired sample volume from the vial.

Next, vertical position motor 394, pivot motor 414, the vertical position motor and the mixer motor are sequentially energized to raise the aspirator assembly, pivot it into its rinsing position 314B, lower it to submerge it in rinsing solution in container 322, and to thereafter rotate mixing sleeve 360. After completion of the analysis of the sample in sample cell 4 which had previously been withdrawn from the vial at position 310A, to pump 58 purges all sample remnants from suction tube 46, tubing 40 and the sample cell by flowing rinsing solution therethrough. Preferably, rotation of the mixing tube 352 continues while the rinsing solution is withdrawn from the container but may cease for commencement of the withdrawal or during the withdrawal of the rinsing solution if that is considered advantageous.

Upon the completion of the rinsing step pump 58 is de-energized and the above-described steps are repeated to immerse the aspirator assembly in the vial at position 310C to withdraw a fresh sample from that vial. After the withdrawal of the sample the aspirator assembly is returned to the rinsing container for rinsing and purging all sample remnants.

As soon as the aspirator assembly has been retracted from the vial at location 310C, or while the assembly is immersed in the container 322, tray drive motor 452 advances index plate 440 by one notch. As crank wheel 462 rotates, mounting plate 456 pivots in a clockwise direction while drive pin 464 rotatably advances the index plate 440. This advance dislodges detent wheel 444 from the notch it previouslyengaged and thereby pivots detent plate 446 in a clockwise direction as the detent wheel rolls over the ridge 443 between adjoining notches. Spring 450 biases the detent wheel into the next adjoining notch. At about that point, drive pin 464 becomes disengaged from the notches and further advance of the index plate ceases. With the engagement of the next notch by the springloaded detent wheel, the next set of vials is at positions 310A and 10C and aligned with the aspiration station.

The pivotal motion of mounting plate 456 is transmitted to index arm 468 and moves pointer 470 into registration with optical sensor 466, thereby signalling that the vial holder has been advanced to present the next set of vials at the aspiration station. The output of sensor of 466 is used to de-energize tray drive motor 452 with the appropriate time delay to permit drive pin 464 to complete one full revolution and to return to its home position.

It will also be noted that the exact alignment of the next set of vials with the aspiration station is accomplished by detent wheel 444 and not by drive pin 464 so that there is considerable lattitude for the drive pin to under or overtravel so long as it is assured that the detent wheel in fact rides over the ridge 443 between the notch it previously engaged and the adjoining notch and so long as the drive pin does not advance the index plate by so much that the index wheel rides over an additional ridge and comes to rest in the following notch.

The aspiration of samples from the new set of vials at the aspiration station now continues in the above-described manner, all steps being repeated until samples have been withdrawn from all vials on holder 306.

A suitable indicator such as a magnetic switch 498 (shown only in FIG. 17) can be provided which is activated by a magnet in a "last vial" on the holder (not shown) to generate a signal that can be used to deactivate the further operation of the sampler 7 of the invention until vials with fresh samples have been placed in the holder. To speed up the replacement of vials the discs 326, 328 of the vial holder can be constructed as a unit that can be lifted off shaft 330 and replaced with another unit already filled with the next set of vials to enable a substantially continuous operation of the sampler and to minimize downtimes.

With the foregoing description of the construction and operation of sample holding cell 4, the associated flow system 6, sampler 7 and optics 8, the construction and operation of system electronics 18 can be described in greater detail. Referring now to FIGS. 7A and 7B, taken together they form a system block diagram of system electronics 18 that controls the operation of the present invention. A table of preferred component types will be set forth below. The central component of the system electronic circuitry is a primary microprocessor 130 which interfaces to system memory, peripherals, and other subassemblies as will be described below. Microprocessor 130 is driven by a 4 MHz crystal clock 131. Microprocessor 130 communicates to other portions of the electronics via a 12-bit address bus 132 (designated AD0-AD11) and an 8-bit system data bus 135 (designated DB0-DB7). Data bus 135 is time multiplexed so that it carries high order address and status information during a first portion of the microprocessor execution cycle and data during the latter portion of the cycle. The high order address information (designated AD12-AD15) is latched at a quad-D flip-flop 137 by the NADS processor strobe and used to drive a 4-to-16 decoder 140 for selecting a particular device (memory unit, peripheral, etc.) for input or output. Some of the decoder outputs are used as strobes to actuate various system functions while other strobes originate directly at microprocessor 130. In addition, a number of logic gates, not shown, are used to coordinate such strobes with other status information in order to achieve correct device selection and control. Thus, address bus 132 provides microprocessor 130 with 12 dedicated address lines (designated AD0-AD11) which, in conjunction with the 4 bits latched by flip-flop 137, provide a total of 16 address lines.

Microprocessor 130 has self-contained inputs and outputs for control of peripheral devices. The outputs consist of three flags (designated FL0, FL1, FL2) and a serial port intended for serial data communication. The inputs consist of two sense inputs (designated $S_A$ and $S_B$) and a serial in port which is not used. Microprocessor 130 is interfaced to an arithmetic processor 145 by two quad D input latches 147 and 148 and a 6-bit tri-state output buffer 150. The interface is a synchronous. Arithmetic processor 145 provides an interrupt signal on a line 152 to sense input $S_A$ of microprocessor 130 in order to allow microprocessor 130 to respond to arithmetic processor 145 during execution of a mathematical operation. One of the outputs of latch 148 communicates to pump driving circuitry 59 for activating pump 58.

System memory comprises random access memory units 160 and 162 (hereinafter sometimes RAM's) that together provide 1024 8-bit bytes of read/write memory, and read-only memory units 165, 167, 168, and 170 (hereinafter sometimes ROM's) that together provide 8192 bytes of read-only memory. The system memory units are coupled directly to address bus 132, and are coupled to a memory interface data bus 172 which is coupled to system data bus 135 through bidirectional tri-state buffers 175 and 177, the operations being controlled by the NRDS and NWDS strobes of microprocessor 130. Bus 172 also communicates to sequencing circuitry 28 to allow microprocessor 130 to control sample retrieval. Sequencing circuitry 28 is selected by appropriate control lines from decoder 140 and associated logic gates in addition to the NWDS and NRDS strobes. Sequencing circuitry 28 is preferably microprocessor controlled, and will be described below. Bus 172 also connects to an IEEE 488 interface card 179 which allows the apparatus of the present invention to communicate to a central computer which could accumulate data from multiple instruments for statistical or other purposes.

Microprocessor 130 is interfaced directly to photon counting electronic circuitry 16 via 1-bit data lines 121, 122, 127, 128, and 129, and 8-bit data line 126. Line 126 carrying counter data is coupled to processor data bus 135 while carry line 122 is coupled to sense input $S_B$. Counter clearing line 121 and carry clearing line 129 are coupled to respective outputs of decoder 140, count enabling line 128 is coupled to flag FL0, and data select line 127 is coupled to address line AD0 of address but 132. Thus, the numerical contents of the BCD counters and the state of the carry flip-flop may be read by microprocessor 130, and signals may be sent in order to clear the counters, clear the carry flip-flop, and enable the counters.

Microprocessor 130 communicates with display 22 through appropriate multiplexing circuitry in display control circuitry 21. Microprocessor 130 and display controller 21 are synchronized by a 7.8 kHz derivative of microprocessor clock 131 provided by a divide by 512 network 200 which drives the display multiplexing circuitry. Display 22 is capable of displaying 16 5×7 dot matrix alphanumeric characters which are refreshed at the rate approximately 70 Hz. Data for the display, consisting of 16 sequentially output ASCII characters, is stored in RAM's 160 and 162 and subsequently read out onto data bus 135 and latched by microprocessor 130 at a latch 205. The display circuitry then accesses this data by strobing a count update line 207 to transfer the data latched at latch 205 to a latch 210. Blanking of the display is controlled by flip-flop 212 which in turn is controlled by strobes from decoder 140.

Microprocessor 130 interfaces to printer 24 through appropriate printer controller circuitry 23. The printhead of printer 24 is an impact dot matrix type utilizing seven solenoid actuated strikers and a motor-driven carriage to move the solenoids across the paper. Paper feed is accomplished by a feed solenoid and friction drive to provide a print speed of 2.3 lines per second. The printer control circuitry is preferably microprocessor based and receives ASCII input data into a 20-position buffer and then controls the motor drive and solenoid firing to form the corresponding characters. Six data lines for ASCII characters, a "print out" line and a "feed out" line for printer control circuitry 23 are coupled to the output of latch 205.

FIG. 8 is a plan view illustrating keyboard 16. Keyboard 26 consists of an array of 28 printed circuit mountable switches arranged as seven columns by four rows. The switches are of the mechanical contact type and are hermetically sealed at the front panel of the instrument by a rubber gasket to prevent leakage of spilled fluids into the instrument. The keyboard switches are used by the operator to enter assay parameters, standards concentrations, and to execute system commands. In particular, keyboard 16 comprises 11 numeric keys 230 (0-9 and decimal point), a clear key 232, 8 concentration units keys 235 (mg/dl, µg/dl ng/dl, %, miu/ml µiu/ml, ng/ml, and pg/ml), four mathematical reduction keys 237 (linear interpolation, reciprocal, hyperbolic, and logit-log), and four system command keys consisting of an ENTER key to 240, a RUN key 242, a PUMP key 245, and a FEED key 247. A "reset" switch is mounted at a separate front panel location and communicates to reset circuitry 250 for providing a reset pulse to microprocessor 130. Two high order lines of address bus 132 communicate to a decoder 252 which supplies four output lines corresponding to the four rows. Seven lines corresponding to the seven columns communicate via a tri-state buffer 255 to processor data bus 135. Thus, the keyboard is scanned by sequentially addressing each keyboard row with a low strobe from decoder 252. Presence of a closed keyboard switch is detected by enabling buffer 255 and reading the keyboard columns. A low on a given line into buffer 255 indicates closure of a switch in the corresponding column while the specific row of that column is determined by the status of the two address lines input to decoder 252.

While many types of integrated circuit components could be used, preferred components are set forth in the following table, designated Table 1.

TABLE 1

| Reference Numeral | Description |
| --- | --- |
| 102 | OP AMP BI-FET LH0062CH |
| 104 | Comparator LM360H |
| 108 | Decade Counter 74LS160N |
| 110 | Decade Counter 74LS160N |
| 112 | Decade Counter 74LS160N |
| 114 | Decade Counter 74LS160N |
| 120 | JK Flip-flop 74LS73N |
| 124 | Quad 2-Data Selector/Multiplexer 74LS257N |
| 125 | Quad 2-Data Selector/Multiplexer 74LS257N |
| 130 | Microprocessor 8-bit INS8060 (National) |
| 137 | Quad Latch 74LS75N |
| 140 | 4-to-6 Decoder/Demultiplexer 74LS154N |
| 145 | Processor 6-bit MM57109 |
| 147 | Quad Latch 74LS75N |
| 148 | Quad Latch 74LS75N |
| 150 | Hex Buffer 74LS365N |
| 160 | 1024x4K Static RAM P2114 |

TABLE 1-continued

| Reference Numeral | Description |
| --- | --- |
| 162 | 1024x4K Static RAM P2114 |
| 165 | 2048x8 EPROM B2716 |
| 167 | 2048x8 EPROM B2716 |
| 168 | 2048x8 EPROM B2716 |
| 170 | 2048x8 EPROM B2716 |
| 175 | Octal Buffer 81LS95N |
| 177 | Octal Buffer 81LS95N |
| 205 | Latch 74LS273N |
| 210 | Latch 74LS273N |
| 212 | JK Flip-flop 74LS73N |
| 252 | Decoder 74LS138N |
| 255 | Octal Buffer 81LS95N |

The software for the operation of microprocessor 130 resides in read-only memory units 165, 167, 168, and 170, and is organized into two major subsets. The first subset comprises operating procedure instructions including a main program for executing a standard assay sequence and subroutines for scanning keyboard 26, strobing display 22, operating printer 24, performing the count sequence, and operating pump 58. The second subset comprises data reduction procedures to be described in detail below.

FIG. 17 is a block diagram of sequencing control electronics 28 responsible for controlling the energization of the various sampler motors described above. The central component of sequencing control circuitry 28 is a microprocessor 500 which interfaces to the sampler motors, the sampler optical position detectors, and microcomputer 20 as will be described below. Microprocessor 500 communicates to other portions of the sequencing electronics via three 8-bit data buses 502, 505, and 507, designated DB, P1 and P2, respectively. An external read-only memory unit 510 has its output lines coupled directly to data bus 502 and addresses are latched at two quad D flip-flops 512 and 514. High order address information is provided by two lines from bus 507. Microprocessor 500 is interfaced to microprocessor 130 within microcomputer 20 through an input latch 515 and an output latch 517 that couple primary processor data interface bus 172 to sequencing microprocessor data bus 502 in a bidirectional manner. Microcomputer 20 supplies control signals to input latch 515 and output latch 517 on appropriate control lines 520 and 522, respectively. In a like manner, microprocessor 500 supplies control signals to latches 515 and 517 on appropriate control lines 525 and 527, respectively.

The eight data lines forming processor bus 502 are connected to respective sensors for verifying various positioning tasks. These include optical sensors 398 and 400 for detecting the upper and lower positions of the aspirator, optical sensors 420, 422, and 424 for detecting the inner row, outer row, and rinse positions of the aspirator assembly, optical sensors 469 and 466 for detecting the first position and subsequent indexing of the turntable, and magnetic switch 498 for detecting a bar magnet placed in the last vial of a sequence to signify the last sample. A "load" switch 529 communicates a logical level to microprocessor 500 on a separate control line 530.

Mixing motor 366, aspirator motor 394 (up/down), motor 414 (left/right), and tray drive motor 452 are controlled by electrical signals on four lines of data bus 507, which signals activate appropriate motor driving circuitry shown schematically at 530. In the preferred embodiment, such circuitry for a given motor includes a transistor switch and a relay which, when energized, communicates 115 volt 60 Hz power to the motor.

While many types of integrated circuit components can be used, preferred components are set forth in the following table, designated Table 2.

TABLE 2

| Reference Numeral | Description |
| --- | --- |
| 500 | Microprocessor 8035 (Intel) |
| 510 | EPROM 2758 |
| 512 | Quad latch 74LS75N |
| 514 | Quad latch 74LS75N |
| 515 | Octal D Latch 74LS374N |
| 517 | Octal D Latch 74LS374N |

When power is first supplied to sequencing electronics 28, microprocessor 500 executes a routine which moves aspirator arm 314 to the rinse position as determined by optical detector 424 and rotates vial holder 306 to the predetermined first position as determined by optical sensor 469. Such movement of the aspirator assembly occurs when microprocessor 500 activates the appropriate one of motors 394 and 414 until the appropriate position sensor provides a signal, the motor being run until a change in the interruptor status signals that the desired location has been reached. Microprocessor 500 then latches a "READY" code at output latch 517 to communicate to microcomputer 20 that sampling may occur. Following this, the command at input latch 515 is ready by microprocessor 500 to determine what action is to be taken. Typically a "DO NOTHING" command will be latched by microprocessor 130 unless microprocessor 500 has latched the "READY" command.

The standard assay sequence includes a calibration sequence and a sample sequence. Prior to counting the fluorescence of test samples, the fluorescence of a number of standard samples, say 10 or 12, of known concentration is measured and a dose response curve is calculated. Thereafter, for the measured fluorescence of a sample, the antigen concentration is calculated and printed out.

Turning first to the operation of the device with respect to acquiring the fluorescence count for a given sample (standard or test), the operation of the device may be described as follows. To briefly summarize, when microprocessor 130 is ready to aspirate a sample, it latches a "SAMPLE" command at sequencer input latch 515. When microprocessor 500 reads this command, it lifts the aspirator assembly and moves it to the outer row position. It then energizes up/down motor 394 until down sensor 400 is interrupted. Next, the mixing cycle is executed during which mixer motor 366 is energized to rotate at approximately 4,500 rpm. The sample is mixed for four seconds. Microprocessor 500 delays for about two seconds to clear air bubbles, and then latches an "IN SAMPLING position" code at output latch 517 to signal microprocessor 130 that it can proceed with sample aspiration. Microcomputer 20 then energizes pump 58 long enough so that a sufficient volume of the sample from a vial at aspiration station 320 of sampler 7 (see FIG. 9, not shown in FIGS. 7A and 7B) is drawn (by vacuum) through the intake tubing 44 to completely fill sample cell 4 in the sample housing. Thereafter the computer then de-energizes the pump.

Microprocessor 130 then latches a "RETURN" command at input latch 515 which causes microprocessor 500 to lift the sampling needle and move it back to the rinse beaker. Each time microprocessor 500 receives a "SAMPLE" command, it executes a similar sequence. However, it alternates between the inner and outer rows from one sequence to the next and rotates the turntable one position after both the inner and outer tubes have been aspirated.

The last vial of the run is indicated by the special magnetic "LAST SAMPLE" vial which contains a permanent bar magnet. As discussed above, this magnet trips magnetically actuated "last sample" sensor 498. Processor 500 then latches a "LAST SAMPLE" code at output latch 517 and activates an audio transducer circuit (not shown) to alert the operator that the run has been completed.

Load switch 529 is functional whenever a required cycle is not being executed. When the switch is closed, the sampling needle is lifted out of rinse container 322, and the system will not execute any procedures until the switch is opened. Sample loading will not commence if load switch 529 is in the closed position.

With the light source 66 energized, the fluorescent particles in the sample in cell 4 fluoresce and emit fluorescent emissions some of which are directed onto PMT 76. Photodiode 86 and stabilizing circuitry 84 maintain the intensity of the light beam from source 66 constant.

The fluorescent emissions received by the PMT result in a bombardment of the PMT cathode (not separately shown) by photons with each photon resulting in a charge or signal pulse. The discriminator circuit 100 removes from the output of the PMT relatively low amplitude noise signals so that the output from the discriminator circuit comprises substantially only signal pulses with each pulse representing a fluorescent emission photon received by the PMT cathode. These pulses are fed into BCD counter 108.

Microprocessor 130 commences the counting sequence by sending low going strobes on carry clearing line 121 and counter clearing line 129 in order to clear the counters and the carry flip-flop. Microprocessor 130 then sets FL0 high in order to communicate a high signal on counter enabling line 128 to enable the counters and begin the count period. The duration of the count period is determined by a software loop of a fixed number of machine cycles, the machine cycle time being precisely fixed by crystal controlled clock 131. During the count period, microprocessor 130 periodically checks carry flip-flop 120, and if a carry occurs, the microprocessor increments a carry storage register in memory and clears the flip-flop. At the end of the count period, FL0 is set low to stop the count. Microprocessors 130 then reads this data through multiplexers 122 and 125 and adds it (4 BCD digits) to the number of carries multiplied to 10,000 to obtain the total number of counts during the count period. Counting continues for an exact, constant predetermined length of time, say two seconds as determined by the processor clock. At the end of the two second time period, counting is discontinued and the total count is further processed as is described below.

Upon the termination of the photon count computer 20 energizes pump 58 again which now draws rinsing solution into the intake tubing 44 from the rinsing container 322 at the aspiration station 320 (FIG. 9). The pump remains energized until at least the entire sample cell 4 is filled with rinsing solution. Drawing the rinsing solution into the sample cell causes the discharge of a corresponding volume of already tested sample fluid through the discharge hose 56 to discharge point 54 and, for example, into an appropriate waste fluid container (not shown).

Thereafter, the pump draws a fresh sample into the sample cell 4 as above-described, while a corresponding volume of the rinsing solution is discharged via the discharge hose.

Having described the operation of aspirating and measuring the fluorescence of a given sample, the overall operation of the apparatus by the operator may be understood. Operation of the apparatus in order to carry out a standard assay procedure is best understood with prior reference to the key functions of the various keys illustrated in FIG. 8.

Numeric keys 230 are used to key in numeric assay parameters (precision and multiplicity) and standards values. The maximum number of digits or alphanumeric characters which may be entered is 14. The numerial "1" key performs a special function which allows the user to halt the system during the run. In order to achieve this function the user must depress and hold the numerial "1" during printout of either the standards results or a sample result. The system scans the keyboard immediately following the printout sequence. The system remains stopped until RUN key 242 is depressed.

CLEAR key 232 is used to erase values from the system memory, if a keying error is made. When CLEAR key 232 is depressed and released, the display and corresponding active location in system memory are cleared to 0. Number entry may then be corrected by depressing the appropriate numeric and concentration keys. Clear key 232 may also be used in a memory modification procedure to delete a bad point from the standard curve by clearing the coorresponding data from the system memory.

Concentration units keys 235 are used to key in concentration units during entry of standards values. When the user depresses the key labeled with a particular concentration unit appropriate for the assay, previously entered numerical values are left shifted by six spaces in the display unit, and the selected concentration units are stored in the rightmost six spaces. The concentration unit is stored in system memory.

Data reduction keys 237 are used to let the user select a data reduction mode in the event that automatic data reduction selection is not desired.

ENTER key 240 is used to enter assay parameter and standard values in system memory. After an assay parameter or standard value has been keyed into the display using numeric keys 230 and concentration keys 235, it may be entered to memory by depressing ENTER key 240. This causes the display value to be entered into memory and printed. This also has the effect of incrementing the memory location pointer so that the next memory storage location becomes available for another value to be keyed in and entered. The ENTER key is also used to access memory locations for modification of values or clearing of a location which is to be deleted.

RUN key 242 is used to command the system to begin loading of standards and/or samples. Pressing this key after entry of all standards causes the system to display the instruction "LOAD STANDARDS" and pressing the key again causes the system to begin aspirating and counting standards and samples. If the system is halted during the assay by use of the numeric "1" key, the run may be continued by pressing RUN key 242.

PUMP key 245 provides a start/stop function for pump 58. One press of the key starts the pump, a second press stops the pump. This key is used to run the pump for the purpose of flushing the system.

FEED key 247 causes the printer to feed the paper forward when the key is depressed to enable the user to format the printout.

Having described the above key functions provided by the system software, the operation of the instrument during a standard assay procedure may now be understood. Initially, vials 310 containing the standards and the test samples to be assayed are loaded into the sample holder 306 for subsequent sequencing. In particular, the samples are loaded so that the standards are measured first for calibration, and the samples to be assayed are measured next. During the initialization, the message "ENTER PRECISION" is displayed on display 22. The operator responds to this prompt by entering via numeric keys 230 the desired allowable percentage deviation of replicates from one another. After the desired value has been keyed in, the operator pushes ENTER key 240, at which point the system prints out the entry and provides an "ENTER # REPLICATES" prompt. The operator responds by keying in either 1 or 2 which will cause samples to be calculated singly or in pairs where pairs of samples are treated as duplicates so that their agreement may be checked. The operator then presses ENTER key 240, and is provided with an "ENTER STANDARD" prompt.

In response to the "ENTER STANDARD" prompt on display 22, the operator enters the concentrations of the standards into system memory in the order in which they were loaded onto the sample holder. Each concentration is keyed in, and upon verifying the entry on the display, the operator presses ENTER key 240 to store the value in memory and increment the memory pointer. A maximum of 16 standard entries is typical. Upon entry of a given standard concentration, the entry is printed out as it is stored, so that after all standards are entered, the operator may check the print out to ensure that the values are correct. The system provides the operator with the ability to correct an incorrect entry.

After the operator has entered and verified all standard concentrations, he presses RUN key 242 in response to which display 22 provides a "LOAD STANDARDS" prompt. The operator verifies that aspirator assembly 318 (and therewith intake tubing 44) communicates with, i.e. is immersed in the first vial 310 of the standard vial set and, upon verification, presses RUN key 242 again. The system now aspirates and counts all of the standard samples. After counting the fluorescence from the standards, the system prints out the concentrations and corresponding counts for all standards. In the event that non-automatic data reduction is desired, the operator halts the system by depressing and holding the numeral "1" key during the print out. In this mode, the operator then selects one of the four data reduction routines by depressing one of data reduction keys 237 corresponding to the four routines. In general, the routine giving the highest correlation value should be used. The operator may eliminate a bad standard sample from the calculation by modifying the memory locations to zero out the concentration of the standard to be eliminated. If automatic data reduction is desired, the system automatically performs the data reductions by running the reciprocal, hyperbolic, and logit-log routines and determining which provides the highest correlation coefficient.

After the calibration parameters have been determined, the system aspirates and counts the test samples sequentially as above discussed, and subsequently prints out the counts, the sample number, and the calculated sample concentration for each sample.

With respect to the second subset of the system software relating to data reduction procedures, such software provides the capability for microprocessor 130 to run in tandem with arithmetic processor 145 to execute standard curve fitting routines and calculate and evaluate results. In all, four curve fitting procedures are available—namely reciprocal, hyperbolic, logit-log, and linear interpolation. In all cases, the routine has as input a set of points $[(u_i, v_i)\ i=1,n]$ where $u_i$ is the concentration of the $i^{th}$ standard sample and $v_i$ is the number of counts for the $i^{th}$ standard sample.

In each of the first three procedures, the data is transformed to a new set of data points $[(x_i, y_i)\ i=1,n]$ and a least-squares fit of the transformed data to the functional form $y = Ax + B$ is carried out. This is a straight line of slope A and intercept B. The slope A, the intercept B and the correlation coefficient R are calculated as follows:

$$A = \frac{\overline{(xy)} - \overline{(x)}\overline{(y)}}{\overline{(x^2)} - \overline{(x)}^2}$$

$$B = \overline{(y)} - A\overline{(x)}$$

$$R = \left[ \frac{[\overline{(xy)} - \overline{(x)}\overline{(y)}]^2}{[\overline{(x^2)} - \overline{(x)}^2][\overline{(y^2)} - \overline{(y)}^2]} \right]^{\frac{1}{2}}$$

where:

$$\overline{x} = \frac{1}{n} \sum_{i=1}^{n} x_i$$

$$\overline{y} = \frac{1}{n} \sum_{i=1}^{n} y_i$$

$$\overline{(x^2)} = \frac{1}{n} \sum_{i=1}^{n} x_i^2$$

$$\overline{(y^2)} = \frac{1}{n} \sum_{i=1}^{n} y_i^2$$

$$\overline{(xy)} = \frac{1}{n} \sum_{i=1}^{n} x_i y_i$$

For the reciprocal procedure, the transformation is:

$x_i = u_i$ $y_i = 1/v_i$ so that the relationship between concentration u and counts v is $1/v = Au + B$.

For the hyperbolic procedure, the transformation is:

$x_i = \ln u_i$ $y_i = \ln v_i$ so that the relationship between concentration u and counts v is $\ln v = A \ln u + B$, or equivalently, $v = Cu^A$ where $\ln C = B$.

For the logit-log procedure, the transformation is:

$x_i = \ln u_i$
$y_i = \text{logit}(v_i/b_0)$
$\quad = \ln \frac{v_i}{b_0 - v_i}$ where $b_0$ is the count for a zero dose. Thus, in order to execute this procedure, a zero standard ($b_0$) must be entered and counted. The zero standard counts must be greater than the counts for the other standards and samples in the set. If a given standard sample has counts greater than $b_0$ (the zero standard), the point will be eliminated from the standard's data automatically. In the event that a sample being assayed gives counts greater than $b_0$ and logit data reduction is being used, the sample will be flagged and the display will show "UNDER RANGE".

Once a given curve has been fitted, concentration values are calculated for each curve point using the curve fit parameters. A check on standard curve validity is accomplished by requiring the computed correlation coefficient to exceed a prescribed minimum value. If this condition is not met the system will halt all operations.

It can thus be seen that the goodness of the fit depends on how well the particular transformation linearizes the data. While the above three procedures provide very good fit for many types of assay, there are certain situations where the transformed data points do not fit a straight line to the required precision. In such a situation, the operator may instruct the computer to use a linear interpolation procedure in which the curve is fitted is a sequence of straight line segments joining adjacent points. Such a fit is not actually a fit since the curve is guaranteed pass exactly through all the data points.

After the particular data reduction routine to be applied to the samples has been determined (automatically on the basis of the highest correlation coefficient, or manually by the operator), the slope and intercept parameters for the selected routines are computed and stored in memory. Thereafter, when samples are assayed and their counts determined, concentrations are calculated using these parameters.

We claim:

1. A fluorescence immunoassay system for sequentially quantitating relatively small amounts of a clinically significant composition in a multiplicity of independent liquid samples, the samples including fluorescent particles, comprising:

transparent means defining a hollow cell for holding the sample;

a light source for generating a stable light beam directed onto the sample;

whereby the light beam causes fluorescent emissions by the particles in the sample, the intensity of the emissions being a function of the intensity of the light beam and the quantity of fluorescent particles in the sample;

means in optical communication with the transparent means for detecting photons resulting from fluorescent emissions by the particles when excited by the light beam;

whereby the number of photons detected by the photon detecting means is a function of the number of fluorescent particles in the sample;

sampler means for sequentially aspirating a liquid from a multiplicity of upwardly open vials, each vial holding one sample;

means for flowing the aspirated liquid to the cell; and means for agitating the sample in the vial prior to aspirating the sample from the vial to ensure a uniform distribution of fluorescent particles in the aspirated liquid.

2. System according to claim 1 wherein the hollow cell has a plurality of mutually perpendicular outer surfaces, one of the surfaces facing the light source and being perpendicular to the light beam.

3. System according to claim 1 including a power supply for the light source, means for sensing the intensity of the beam, and circuit means operatively coupled with the sensing means and the power supply for adjusting the output of the power supply in response to changes in the intensity of the light beam so that the light beam intensity remains substantially constant.

4. System according to claim 3 wherein the sensing means comprises a photodiode, and wherein the circuit means includes means for amplifying an output of the photodiode, means for comparing the amplified output of the photodiode with a reference signal to generate a difference signal, and means for applying the difference signal to the power supply to correspondingly adjust its output to the light source.

5. System according to claim 4 wherein the light source comprises a tungsten-halogen incandescent lamp and the photodiode comprises a silicon photodiode.

6. System according to claim 4 including filter means between the light source and the sample for conditioning the light beam so as to minimize light scattering and enhance fluorescent emissions by the particles, and wherein the photodiode is positioned relatively proximate to the transparent means and optically downstream of the filter means.

7. System according to claim 1 wherein the flowing means comprises an inlet to and an outlet from the cell, wherein the sampler means includes an aspirator for withdrawing the liquid samples from the sample vials, and further including intake tubing fluidly communicating the aspirator with the inlet; discharge tubing fluidly communicating the outlet with a sample discharge point, and a pump located downstream of the outlet for intermittently flowing a sample from the aspirator to the cell, for maintaining the sample in the cell for a period of time, and for thereafter removing the entire sample from the cell and the intake tubing and replacing the removed sample with a fresh sample; whereby the sample is not subjected to the flow inducing action of the pump until after it has passed the cell.

8. System according to claim 7 wherein the sampler means includes a container holding a rinsing solution, and including means for alternatively fluidly communicating the aspirator with the vials and the container.

9. System according to claim 8 including means for alternatingly fluidly communicating the aspirator with the vial and the container in response to each operation of the pump so that at least the intake tubing and the cell is cleaned with the rinsing solution prior to the replacement of the sample with the fresh sample.

10. System according to claim 1 wherein the photon detecting means includes means for generating signal pulses for individually sennsed photons, and further including digital pulse counting means having an input in communication with the signal pulse generating means for producing a numeric code representative of the number of pulses received at the input.

11. System according to claim 10 wherein the pulse counting means includes an enable input, and further including processor means coupled to the pulse counting means, the processor means having means for receiving and storing the numeric code from the pulse counting means, the processor means also having means for enabling the pulse counting means for a predetermined interval of time so that the numeric code stored is representative of concentration of the clinically significant compound.

12. System according to claim 11 wherein the processor includes means for storing the known concentrations of the clinically significant compound for a plurality of standard samples, means for storing a corresponding plurality of numeric codes corresponding to the measured fluorescent activity of the plurality of samples having known concentration, and arithmetic means for computing a calibration curve on the basis of the plurality of known concentrations and the plurality of numeric codes.

13. System according to claim 12 wherein said arithmetic means includes means for computing a calibration curve according to at least two mathematical hypotheses, and for choosing the mathematical hypothesis that provides the highest correlation coefficient.

14. System according to claim 1 wherein the photon detecting means includes means for generating signal pulses for individually sensed photons, and further comprising:
digital pulse counting means for receiving the signal pulses from said photon detecting means and for providing a numeric code output representative of the number of pulses counted; and
programmed microcomputer means in communication with the pulse counting means, the programmed microcomputer means having means for selectively enabling the counting means for a predetermined time interval such that the numeric code from the counting means is representative of the concentration of the clinically significant compound, the microcomputer means having means for storing known concentration information for a plurality of standard samples and means for accumulating and storing count information corresponding to said plurality of standard samples, the microcomputer having means for determining a calibration curve on the basis of the known concentrations and count information according to at least two mathematical hypotheses and for selecting the calibration curve that provides the best correlation coefficient.

15. System according to claim 1 wherein the sampler means comprises:
an aspirator including an upright, downwardly opening suction tube for sequential insertion into the vials;
tray means supporting the vials for incrementally moving the vials to an aspiration station;
positioning means for aligning the suction tube and the vial at the aspiration station; and
immersion means for vertically moving the suction tube into and out of a vial at the station so as to immerse a lower end of the tube in the sample in such vial.

16. System according to claim 15 wherein the agitating means comprises a rotary mixer carried by the aspirator.

17. System according to claim 16 wherein the mixer comprises a tubular member concentric with the suction tube, means for rotating the tubular member about its axis, and means for maintaining the suction tube stationary.

18. System according to claim 19 wherein the suction tube is disposed within the tubular member.

19. System according to claim 18 wherein the aspirator includes a frame, wherein the suction tube is fixedly mounted to the frame, and including means for rotatably mounting the tubular member to the frame.

20. System according to claim 19 wherein the tubular member has a lower end protruding past a corresponding end of the suction tube.

21. System according to claim 20 wherein the lower end of the tubular member is defined by a cylindrical wall, and including at least one downwardly opening groove in the cylindrical wall to facilitate the agitation of the liquid in the vial.

22. System according to claim 15 wherein the immersion means comprises an upright rod having an upper end to which the aspirator is mounted, and means for vertically reciprocating the rod so that the lower end of the suction tube is above an upper end of the vial at the aspiration station when the rod is in its raised position and immersed in the sample and proximate but spaced from a bottom of the vial when the rod is in its lowered position.

23. System according to claim 22 including first drive means for vertically reciprocating the rod comprising a rack and pinion drive including a load reversible electric motor for rotating the pinion of the drive and for reversing its rotational direction whenever the rod encounters a torque of a predetermined magnitude which opposes the continued movement of the rod in a given direction; whereby misalignments and an interference between the suction tube and objects including the vial at intermediate positions of the reciprocating rod automatically terminates further movement of the rod and of the suction tube in such direction and thereby prevents damage to the apparatus and the vial.

24. System according to claim 23 including optical limit switches operatively electrically coupled with the electric motor for sensing raised and lowered positions of the rod and for de-energizing the electric motor in response to sensing the presence of the rod in either one of said positions to prevent further travel of the rod in a given direction.

25. System according to claim 15 including a container holding a rinsing solution for rinsing the interior and the exterior of the suction tube after the sample in the vial has been withdrawn to prevent contamination of the sample in the next vial to be aspirated by the sample from the previously aspirated vial, wherein the positioning means includes means for aligning the suction tube with the container, and wherein the immersion means includes means for vertically moving the suction tube into and out of the container when the container and the tube are in alignment.

26. System according to claim 25 wherein the tray means includes a tray having means for holding the vials, and means for moving the tray along a predetermined path past the aspiration station, and wherein the positioning means includes means for arresting movement of the tray means when a vial is at the aspiration station.

27. System according to claim 26 wherein the tray means includes means for rotating the tray about an axis and means for mounting the vials to the tray in a general circular pattern concentric with respect to the tray axis, and wherein the tray moving means comprises means for rotatably moving the tray in fixed increments about its axis so as to present a vial at the aspiration station after an incremental movement of the tray.

28. System according to claim 27 wherein the vial holding means includes means for arranging the vials in a plurality of concentric, radially spaced rows; and wherein the positioning means includes means for moving the suction tube in a direction transverse to the direction of movement of the vials past the aspiration station into alignment with a plurality of vials which equals the plurality of rows while the tray remains stationary.

29. System according to claim 28 wherein the means for moving the suction tube comprises a frame for mounting the tube and means for pivoting the frame about an aspirator axis parallel to the suction tube between a first position in which the tube is aligned with a vial at the station in a first row and a second position in which the tube is in alignment with a vial at the station in the second row.

30. System according to claim 29 wherein the vial mounting means includes means arranging the vials at the aspiration station so that centers of such vials substantially lie on a circularly arcuate line having as its origin the aspirator axis.

31. System according to claims 30 wherein the container is positioned on the arcuate line, and wherein the means for aligning the suction tube with the container comprises means for pivotally moving the frame about the aspirator axis until the suction tube is in substantial alignment with the container.

32. System according to claim 31 wherein the positioning means includes second drive means for pivotally moving the frame about the aspirator axis, the second drive means including signal means for indicating when the tube is in alignment with any one of the container and the vials at the aspiration station, and means responsive to the signal means for arresting the pivotal movement of the frame when the suction tube is in alignment with a vial or the container into which the suction tube is to be moved.

33. System according to claim 32 wherein the immersion means includes first drive means having an upright rod connected with the aspirator, the rod being aligned with and mounted to rotate about the aspirator axis; and wherein the second drive means includes a crank drive operatively coupled with the rod and having a drive wheel, the crank drive being arranged so that one rotation of the drive wheel causes a pivotal movement of the frame and therewith of the suction tube from a given point along said arcuate line over all other points on said line and back to said given point.

34. System according to claim 15 wherein the tray means includes vial holding means arranging the vials in at least one circular row, means mounting the vial holding means for rotation about an upright tray axis so that rotation of the vial holding means sequentially presents the vials at the aspiration station, and a notched index wheel fixedly connected with the vial holding means and rotatable therewith, the index wheel having a number of notches corresponding to the number of positions of the vial holding means at which a vial is presented at the aspiration station, and wherein the positioning means comprises a detent, and spring means resiliently biasing the detent into engagement with the notches, the detent being positioned so that a vial is aligned with the suction tube at the aspiration station when the detent fully rests in a corresponding notch in the index wheel.

35. System according to claim 34 wherein the tray means includes third drive means operatively engaging the index wheel for incrementally advancing the index wheel to sequentially engage the notches on the index wheel with the detent.

36. System according to claim 35 wherein the notches in the index wheel are radially oriented, and wherein the detent is biased towards the index wheel in a radially inward direction.

37. System according to claim 35 wherein the third drive means comprises drive pin means having a surface shaped to engage the notches in the index wheel and mounted adjacent of the index and means for moving the surface to engage a notch on the index wheel and rotatably advance the index wheel to engage the detent with another notch and to thereby align another vial with the suction tube at the aspiration station.

38. System according to claim 37 wherein the cam surface is eccentrically mounted to a rotatable cam wheel, and including means for resiliently biasing the surface towards the index wheel, and means limiting the extent to which the surface can move towards the index wheel so that the surface engages the index wheel during only a portion of the rotation of the cam wheel.

39. System according to claim 38 wherein the third drive means includes means for rotating the cam wheel through one full revolution for rotatably advancing the index wheel through an arc no greater than the arc between adjoining notches.

40. A system for performing fluorescence immunoassay on a multiplicity of individual liquid test samples including fluorescent particles and stored in a like multiplicity of relatively long, upright, upwardly open vials for quantitating relatively small amounts of a clinically significant composition comprising:
a vial holder holding the vials in an upright position and arranging the vials in at least one row;
advancing means for moving the vial holder to present each vial at an aspiration station; an aspirator including a frame, a vertically oriented suction tube fixedly mounted to the frame;
an upwardly open container spaced from the rows and located proximate the aspiration station for holding a volume of a rinsing solution;
positioning means for moving the frame to alternatively substantially vertically align the suction tube with a vial at the aspiration station and with the container;
immersion means for raising and lowering a lower end of the suction tube between a raised position at which the lower suction tube end clears an upper end of the vial at the aspiration station and the container and a lowered position at which the lower suction tube end is immersed in liquid in the tube or the container;
means for operating the positioning means and the immersion means so as to immerse the suction tube in the container after each immersion of the suction tube in a vial at the aspiration station;
a transparent housing defining an interior cell and an inlet and an outlet to and from the cell, respectively;
conduit means including pump means fluidly communicating the suction tube with the cell inlet for flowing a sample from the tube to the cell;
means for holding a portion of each sample for at least a minimum period of time stationarily in the cell;
optical means including a light source generating a light beam which is directed into the cell for causing fluorescent emissions by the particles in the cell, the intensity of which is a function of the intensity of the light beam and the quantity of particles in the cell;
photosensing means for sensing the fluorescent emissions over a predetermined time period and for generating corresponding output signals;
means for stabilizing the intensity of the light beam to prevent substantial variations in the intensity of the light beam from a preset light beam intensity;
discriminator means for eliminating from the output signals at least a substantial portion of any background noise signals which are included in the output signals;
digital counting means responsive to the output signals; and
microcomputer means including
means for receiving and storing numeric information from the counting means,
means for enabling the counting means for a predetermined length of time so that the numeric information is representative of the number of particles in the cell,
means for enabling the pump activating means at a time when the counting means is not enabled so that counting may occur while the sample is stationary in the cell,
means for storing known concentration information for a plurality of standard samples and means for accumulating and storing count information corresponding to said plurality of standard samples, and
means for determining a calibration curve on the basis of the stored known concentrations and count information according to at least two mathematical hypotheses and for selecting the calibration curve that provides the best correlation coefficient.

41. System according to claim 40 including means defining a generally L-shaped optical chamber having perpendicular optical axes; and wherein the cell is disposed at the intersection of the axes.

42. System according to claim 40 wherein the optical means and the photosensing means are disposed in the optical housing and aligned with the first and second optical axes, respectively.

43. System according to claim 42 wherein the transparent housing has a generally square cross-section, the housing including first and second perpendicular sides which are arranged perpendicular to the first and second optical axes, respectively.

44. System according to claim 43 wherein the cell has a square cross-section and includes first and second perpendicular walls which are parallel to the first and second sides of the housing.

45. System according to claim 40 wherein the photosensing means comprises a photomultiplier tube, wherein the output signals comprise signal pulses generated by photons from fluorescent emissions of the particles in the cell and noise pulses; and wherein the discriminator means includes means for eliminating the noise pulses from the output signals before the signal pulses are fed to the processing means.

46. System according to claim 45 wherein the signal pulses have an amplitude greater than the noise pulses, and wherein the discriminator means includes an amplitude discriminator for eliminating the noise pulses from the output signals.

47. System according to claim 40 including indexing means for positioning the vial at the aspiration station, the indexing means being independent of the advancing means.

48. System according to claim 40 wherein the vial holder arranges the vials in at least two side by side, parallel rows; wherein the frame moving means includes means for pivoting the frame about an upright frame axis so that the suction tube moves along a circularly arcuate path; and wherein a vial in each row is simultaneously positioned at the aspiration station.

49. System according to claim 40 wherein the vial holder arranges the vials in a plurality of rows; and including means for aligning a vial in each row with the aspiration station, the aligning means comprising an index member fixedly attached to the vial holder for movement therewith, a detent biased towards the indexing member, the indexing member and the detent defining cooperating concave and convex index surfaces, the surfaces being arranged so that upon the mutual engagement of the detent with a corresponding surface on the indexing member a vial in each row is aligned with the aspiration station, the number of surfaces on the indexing means being equal to the number of vials held by the holding means divided by the number of rows.

50. A system for performing fluorescent immunoassay on a multiplicity of individual liquid test samples including fluorescent particles and stored in a like multiplicity of vials for quantitating relatively small amounts of a clinically significant composition comprising: a transparent housing having a square cross-section and including an interior sample cell of a square cross-section, corresponding housing sides and cell walls being parallel to each other, the housing including an inlet to and an outlet from the cell; an intake conduit in fluid communication with the inlet and having an other end; a sampler including an aspirator, a container for holding a rinsing solution and means supporting the vials; means for alternatively aligning the aspirator with a vial or with the container; an intake conduit fluidly communicating the aspirator with the cell inlet; a discharge conduit in fluid communication with the outlet; pump means disposed downstream of the outlet and cooperating with the discharge conduit for flowing a sample or rinsing solution by suction through the intake conduit, the cell and a portion of the discharge conduit and for flowing it to a point of discharge; sequencing means for intermittently activating the pump means and for alternatingly immersing the aspirator in the container and in a vial to alternatingly flow a sample or rinsing solution into the cell; the sequencing means including means for activating the pump means for a sufficient length of time to evacuate the entire liquid in the cell and replace it with fresh liquid from one of the container or one of the vials; an optical housing defining a pair of perpendicular, optical branches defining perpendicular optical axes, the cell being disposed in the optical housing and at an intersection of the axes, a light source in one of the branches for generating a light beam and first optical means disposed in the optical branch between the light source and the cell for removing from the light beam substantially all light other than light of a wavelength which causes the fluorescent particles to emit fluorescent emissions; a photomultiplier in the other branch and second optical means for directing the fluorescent emissions onto the photomultiplier, the photomultiplier generating a signal pulse for each fluorescent transmission photon received thereby and noise signals; the housing including means for preventing light other than fluorescent emissions caused by the direct excitation of the fluorescent particles by the light beam from reaching the photomultiplier;

light beam stabilization means operatively coupled with the light source and including a photosensor disposed in the optical housing proximate the transparent housing and optically downstream of the first optical means for sensing the light beam striking the housing and for adjusting its intensity so that the light beam remains substantially constant;

discriminator means operatively coupled with the photomultiplier for removing the noise signals and for generating output signals comprising substantially only signal pulses;

counting means operatively coupled with the discriminator means for counting the number of signal pulses emitted by the photomultiplier; and microcomputer means having means for enabling the counting means over a predetermined, constant length of time and for forming an output which is an indication of the number of fluorescent particles in the sample cell, the microcomputer means having means operativly coupled with the pump means for deactivating the pump means during at least the predetermined length of time and for activating the pump means during other times so that a tested sample fluid from the cell is removed, the cell is rinsed with rinsing solution, and thereafter a fresh sample is flowed into the cell.

51. A system for performing fluorescent immunoassay on a multiplicity of individual test samples including fluorescent particles and stored in a like multiplicity of vials for quantitating relatively small amounts of a clinically significant composition, the system comprising: a vial holder arranging the vials in at least one row of a predetermined shape and maintaining the vials in an upright position so as to render them accessible from the top; means for intermittently moving the holder parallel to the row to sequentially position the vials at an aspiration station; a container located proximate the aspiration station for holding a rinsing solution; an aspirator frame including at least a portion disposed above uppermost ends of the vials at the aspiration station and an uppermost end of the container; a suction tube affixed to the frame and having an open lower end; flow means in fluid communication with the suction tube for subjecting the tube to a vacuum to draw a liquid through the tube when the lower tube end is immersed in a liquid; a rotary mixer secured to the frame proximate the tube and depending from the tube to a point below the lower tube end, the tube and the mixer being constructed so that they can be simultaneously inserted in a vial; immersion means for reciprocating the frame in a vertical direction over a sufficient distance so that in a raised position of the frame the lower end of the mixer is above the vials and the container and in a lowered position of the frame the lower end of the mixer and the lower end of the tube are immersed in liquid in the vial or the container; positioning means for moving the frame along a predetermined path to alternatively substantially align the tube and the mixer with a vial at the aspiration station or with the container; a transparent housing defining a sample cell having an inlet in fluid communication with the flow means and the suction tube and an outlet; a light source for generating a stable light beam focused on the cell; whereby the light beam causes fluorescent emissions by particles in the cell, the intensity of the emissions being a function of the intensity of the light beam and the quantity of fluorescent particles in the cell; means in optical communication with the transparent housing for detecting photons resulting from fluorescent emissions by the particles when excited by the light beam; whereby the number of photons detected by the photon detecting means is a function of the number of fluorescent particles in the cell; and means for sequentially energizing the holder moving means, the positioning means, the immersion means, the mixer and the flow means to initially align the tube and the mixer with a vial at the aspiration station, to thereafter immerse the sample in the vial at the aspiration station, mix the sample with the mixer and thereafter withdraw at least a portion of the sample from the vial through the tube and flow it to the cell, thereafter withdraw the tube and the mixer in an upward direction from the vial and move them into registration with the container, immerse them in the container and flow rinsing solution from the container and through the suction tube until it at least fills the cell to remove from the tube, the mixer, the flow means and the cell substantially all previous sample remnants, and to thereafter realign the mixer and the tube with another vial at the aspiration station for withdrawing a fresh sample from said another vial; whereby the samples in the vials are uniformly mixed before their withdrawal therefrom and a cross-contamination between samples is prevented.

* * * * *